United States Patent [19]

Willard et al.

[11] 4,375,475

[45] Mar. 1, 1983

[54] SUBSTITUTED PYRANONE INHIBITORS OF CHOLESTEROL SYNTHESIS

[75] Inventors: Alvin K. Willard, Wilmington, Del.; Frederick C. Novello, Berwyn, Pa.; William F. Hoffman; Edward J. Cragoe, Jr., both of Lansdale, Pa.

[73] Assignee: Merck & Co., Inc., Rahway, N.J.

[21] Appl. No.: 233,521

[22] Filed: Feb. 11, 1981

Related U.S. Application Data

[63] Continuation-in-part of Ser. No. 140,323, Apr. 14, 1980, abandoned, which is a continuation-in-part of Ser. No. 67,574, Aug. 1, 1979, abandoned.

[51] Int. Cl.³ .................. A61K 31/365; C07D 309/30
[52] U.S. Cl. .................... 424/279; 542/441; 549/292
[58] Field of Search ..................... 542/441; 260/343.5; 424/279

[56] References Cited

U.S. PATENT DOCUMENTS

| | | | |
|---|---|---|---|
| 3,522,245 | 7/1970 | Brinkhoff | 542/441 |
| 3,600,403 | 8/1971 | Brinkhoff | 542/441 |
| 3,957,440 | 8/1976 | Hajos et al. | 260/338 |
| 3,965,129 | 6/1976 | Perry et al. | 260/348.45 |
| 3,983,140 | 9/1976 | Endo et al. | 260/343.5 |
| 4,198,425 | 4/1980 | Mitsui et al. | 260/343.5 |

FOREIGN PATENT DOCUMENTS

10951 6/1980 European Pat. Off. .
2822848 11/1978 Fed. Rep. of Germany .

OTHER PUBLICATIONS

Brown et al., J. Chem. Soc., Perkin I (1976), 1165–1169.
Hulcher, Arch. Biochem & Biophys, 146, 422–427 (1971).
Singer et al., Proc. Soc. Exper. Biol. Med. 102, 370–373 (1959).
Meyer, Liebigs Ann. Chem. (1979) pp. 484–491.

*Primary Examiner*—Arthur P. Demers
*Attorney, Agent, or Firm*—William H. Nicholson; Mario A. Monaco

[57] ABSTRACT

6-Phenyl-, phenylalkyl- and phenylethenyl-4-hydroxytetrahydropyran-2-ones in the 4(R)-trans stereoisomeric forms are potent inhibitors of cholesterol synthesis by virtue of their ability to inhibit the enzyme, 3-hydroxy-3-methylglutaryl-coenzyme A reductase.

18 Claims, No Drawings

SUBSTITUTED PYRANONE INHIBITORS OF CHOLESTEROL SYNTHESIS

SUMMARY OF THE INVENTION

This is a continuation-in-part of copending application, Ser. No. 140,323 filed Apr. 14, 1980, (abandoned) which in turn is a continuation-in-part of copending application, Ser. No. 067,574, filed Aug. 1, 1979 (now abandoned).

This invention relates to new hypocholesterolemic and hypolipemic compounds having the structure (I)

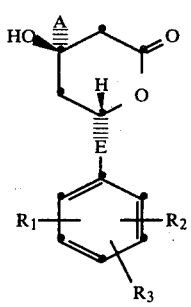

and the corresponding dihydroxy acids resulting from the hydrolytic opening of the lactone ring, and the pharmaceutically acceptable salts of said acids, and the lower alkyl and phenyl, dimethylamino or acetylamino-substituted lower alkyl esters of said dihydroxy acids; all of the compounds being the enantiomers having a 4(R) configuration in the tetrahydropyran moiety of the trans racemate shown in formula I.

BACKGROUND OF THE INVENTION

It is known that certain mevalonate derivatives inhibit the biosynthesis of cholesterol, cf F. M. Singer, et al., *Proc. Soc. Exper. Biol. Med.*, 102, 270 (1959) and F. H. Hulcher, *Arch. Biochem. Biophys.*, 146, 422 (1971). Nevertheless, the activity of these known compounds has not always been found to be satisfactory, i.e. to have practical application.

Recently, Endo et al, reported (U.S. Pat. Nos. 4,049,495, 4,137,322 and 3,983,140) the production of a fermentation product which was quite active in the inhibition of cholesterol biosynthesis. This natural product, now called compactin, was reported by Brown et al., (*J. Chem. Soc. Perkin I*, 1165 (1976)) to have a complex mevalonolactone structure.

A recent Belgian Pat. No. 867,421 disclosed a group of synthetic compounds of the generic formula II

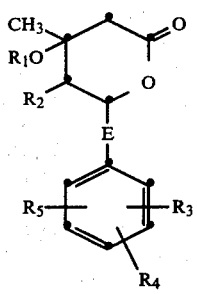

in which E represents a direct bond, a $C_{1-3}$ alkylene bridge or a vinylene bridge and the various R's represent a variety of substituents.

The activity reported in the Belgian patent is less than 1% that of compactin.

DETAILED DESCRIPTION OF THE INVENTION

This invention relates to new hypocholesterolemic and hypolipemic compounds having the structure (I)

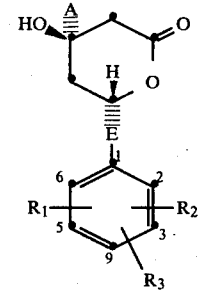

wherein
A is H or methyl;
E is a direct bond, $-CH_2-$, $-CH_2-CH_2-$, $-CH_2-CH_2-CH_2-$ or $-CH=CH-$;
$R_1$, $R_2$ and $R_3$ are each selected from
H,
halogen,
$C_{1-4}$ alkyl,
$C_{1-4}$ haloalkyl,
phenyl,
phenyl substituted by halogen,
$C_{1-4}$ alkoxy
$C_{2-8}$ alkanoyloxy
$C_{1-4}$ alkyl, or
$C_{1-4}$ haloalkyl, and
$OR_4$ in which $R_4$ is
H,
$C_{2-8}$ alkanoyl,
benzoyl,
phenyl,
halophenyl,
phenyl $C_{1-3}$ alkyl,
$C_{1-9}$ alkyl,
cinnamyl,
$C_{1-4}$ haloalkyl,
allyl,
cycloalkyl-$C_{1-3}$-alkyl,
adamantyl-$C_{1-3}$-alkyl, or
substituted phenyl $C_{1-3}$-alkyl
in each of which the substituents are selected from
halogen,
$C_{1-4}$ alkoxy
$C_{1-4}$ alkyl, or
$C_{1-4}$ haloalkyl;
and the corresponding dihydroxy acids resulting from the hydrolytic opening of the lactone ring, and the pharmaceutically acceptable salts of said acids, and the $C_{1-3}$ alkyl and phenyl, dimethylamino or acetylamino-substituted-$C_{1-3}$-alkyl esters of the dihydroxy acids; all of the compounds being the enantiomers having a 4 R configuration in the tetrahydropyran moiety of the trans racemate shown in formula I.

A preferred embodiment of this invention relates to those structures of general formula I wherein A is H or methyl;
E is —CH=CH—, or —CH$_2$CH$_2$—;
R$_1$, R$_2$ and R$_3$ are each selected from
  halogen,
  C$_{1-4}$ alkyl,
  C$_{1-4}$ haloalkyl,
  substituted phenyl in which the substituent is
    halo,
    C$_{1-4}$ alkyl,
    C$_{1-4}$ alkoxy, and
  R$_4$O in which R$_4$ is
    phenyl,
    halophenyl,
    or
    substituted phenyl-C$_{1-3}$-alkyl
    wherein the substituents are selected from
      halogen and
      C$_{1-4}$ haloalkyl;

and the corresponding dihydroxy acids resulting from the hydrolytic opening of the lactone ring and the pharmaceutically acceptable salts of the dihydroxy acids, and the C$_{1-3}$ alkyl and phenyl, dimethylamino or acetylamino-substituted-C$_{1-3}$ alkyl esters of the dihydroxy acids; all of the compounds being the enantiomer having a 4 R configuration in the tetrahydropyran moiety of the trans racemate shown in general formula I.

A more preferred embodiment of the present invention comprises those structures of general formula I wherein A is H or methyl;
E is —CH$_2$CH$_2$— or —CH=CH—;
R$_1$ is situated in the 6-position and is a substituted phenyl wherein there are 1 or 2 substituents and they are independently selected from chloro, fluoro, methyl and methoxy; and
R$_2$ and R$_3$ are halo, especially chloro, or C$_{1-3}$ alkyl, especially methyl, in the 2 and 4 positions;

and the corresponding dihydroxy acids resulting from the hydrolytic opening of the lactone ring, and the pharmaceutically acceptable salts of the dihydroxy acids, and the C$_{1-3}$ alkyl and phenyl, dimethylamino or acetylamino-substituted-C$_{1-3}$ alkyl esters of the dihydroxy acids; all of the compounds being the enantiomer having a 4 R configuration in the tetrahydropyran moiety of the trans racemate shown in general formula I.

The compounds in which A is hydrogen, are especially to be preferred. It is also especially preferred that E is —CH=CH—.

The designation 4 R with respect to these compounds indicates that the absolute configuration in space at the 4 -carbon of the pyranone ring is believed to be the Rectus (R) series. All the compounds synthesized in the (R) series have been found to be dextrorotatory.

It also has been found that the enantiomers of the trans compounds of Formula I having a 4 R configuration in the tetrahydropyran moiety, especially those in which A is hydrogen, E is —CH=CH— and R$_1$ and R$_2$ are Cl or —CH$_3$ in the 2 and 4 position and R$_3$ is substituted-phenyl in the 6 position, as described, are unexpectedly potent inhibitors of cholesterol biosynthesis, approaching and, in many instances, surpassing the order of magnitude of compactin.

While the compounds of Formula I in which A is methyl are 4-R enantiomers of the trans racemates of the compounds of the cited Belgian patent, the latter prior art shows no recognition of the stereochemistry of these compounds, let alone the fact that an unexpectedly large improvement in the activity would result from the separation of the cis and trans racemates and the latter's resolution, especially when the preferred 2,4,6-trisubstitution occurs in the phenyl ring. However, it has been found that the 4 R enantiomers of the trans racemates corresponding to formula I specifically inhibit with high potency the activity of 3-hydroxy-3-methylglutaryl-coenzyme A reductase, which is known to be the enzyme involved in the rate limiting step in the process of cholesterol biosynthesis.

The inhibitory activity of these compounds for the biosynthesis of cholesterol has been measured by two methods. The experimental method A was the in vitro method of H. J. Knauss, et al., *J. Biol. Chem.*, 234, 2835 (1959) and the activity was expressed as the molar concentration IC$_{50}$(M) necessary for the inhibition of 50% of the enzymatic activity. The experimental method B was the method of A. A. Kandutsch, et al., *J. Biol. Chem.*, 248, 8403 (1973) for measuring the quantity of $^{14}$C-cholesterol biosynthesis from acetic acid-$^{14}$C in mouse L cells. The activity is expressed for inhibition of 50% of the biosynthesis of cholesterol.

The results obtained in these two assays, as reported in the cited Belgian patent, show IC$_{50}$ values of 10$^{-4}$ to 10$^{-6}$ in both tests. The smallest 50% effective dose cited is about 4×10$^{-6}$, whereas the value for compactin, in the same tests, is about 0.8×10$^{-8}$. We have found that the inhibitory potency is greatly increased by separation of isomers especially when this is combined with optimal selection of a 2,4,6-arrangement of R$_1$, R$_2$ and R$_3$ in the phenyl ring and especially when A is hydrogen and E is —CH=CH—. Thus the (+) trans enantiomer of 6-[2-(2,4-dichloro-6-(phenylmethoxy)phenyl)ethyl]-3,4,5,6-tetrahydro-4-hydroxy-2H-pyran-2-one (Example 14) (a preferred compound of this invention) gives an IC$_{50}$ of 6.8×10$^{-8}$ in the test by method A. An even more potent and preferred compound of this invention, the (+) trans enantiomer of (E)-6-[2-(3,5-dichloro-4'-fluoro[1,1'-biphenyl]-2-yl)ethenyl]-3,4,5,6-tetrahydro-4-hydroxy-2H-pyran-2-one (Example 43) gives an IC$_{50}$ of about 1.3×10$^{-8}$.

Other preferred compounds are: 6-[2-(4'-fluoro-3,3',5-trimethyl[1,1'-biphenyl]-2-yl)ethenyl]-3,4,5,6-tetrahydro-4-hydroxy-2H-pyran-2-one (IC$_{50}$=7×10$^{-9}$); 6-[2-(5-chloro-4'-fluoro-3,3'-dimethyl[1,1'-bisphenyl]-2-yl)ethenyl]-3,4,5,6-tetrahydro-4-hydroxy-2H-pyran-2-one (IC$_{50}$=6×10$^{-9}$); and 6-[2-(3,3',5,5'-tetramethyl-[1,1'-biphenyl]-2-yl)ethenyl]-3,4,5,6-tetrahydro-4-hydroxy-2H-pyran-2-one (IC$_{50}$=1.5×10$^{-8}$). The compounds were tested as the sodium salts of their corresponding hydroxy acid forms.

The preparation of the compounds of this invention is illustrated in the Flow Sheets.

Flow Sheet I shows the general scheme for synthesizing compounds with a vinylene bridge between the lactone and benzene rings. A starting benzaldehyde is converted to the corresponding cinnamaldehyde (this forms the bridging group) and this is subjected to an aldol reaction to elaborate a hydroxy keto ester from the terminal aldehydic moiety. Reduction of the hydroxy keto ester affords the dihydroxy ester which, upon saponification and subsequent lactonization, gives the lactone. The lactone is then separated chromatographically into its cis and trans racemates and the latter racemate is resolved to give the desired 4 R trans enantiomer.

Flow Sheet II shows the further conversion of the 4 R trans lactones into the corresponding dihydroxy acids and their salts and esters. Although this sequence is shown with the —CH=CH— bridged compounds, the same sequence can be used to give the corresponding acids, salts and esters of any of the other bridged compounds.

Flow Sheet III shows the synthetic routes for the preparation of the alternative bridging groups, represented by E in formula I. Compounds with a direct bond between the lactone and phenyl rings are made by the process of Flow Sheet I with omission of step 2. In this instance, the starting benzaldehyde is used directly in the Aldol reaction. Compounds with a methylene (—CH$_2$—) bridge are prepared by starting with the appropriate phenylacetaldehyde in place of the cinnamaldehyde. Compounds with an ethylene (—CH$_2$—CH$_2$—) bridge between the rings are prepared by reduction of the vinylene bridged compounds prepared in Flow Sheet I. Compounds with a trimethylene bridge (—CH$_2$—CH$_2$—CH$_2$—) are prepared by starting with the appropriate 1-bromo-3-phenylpropane. Compounds of formula I wherein A is a methyl group are prepared as indicated in Flow Sheet IV. Starting with the appropriate aldehyde, condensation with 1-(tri-n-butylstannyl)propan-2-one affords a β-hydroxy ketone which can be converted to the target lactones either by (a) acylation with 2-bromoacetyl bromide followed by intramolecular Reformatsky cyclization or (b) acylation with acetyl chloride followed by intermolecular Reformatsky reaction with ethyl 2-bromoacetate followed by saponification and subsequent lactonization of the resulting dihydroxy acid. Separation of the cis and trans racemic lactones and the subsequent resolution of the trans racemate to obtain the 4 R enantiomer are carried out as described in Flow Sheet I.

Flow Sheet V shows the details of the synthesis of benzaldehydes having an ortho phenyl group, followed by their use in the general scheme of Flow Sheet I to form compounds of this invention. This Flow Sheet summarizes the use of the benzaldehydes so made in the synthesis of vinylene bridged compounds as in Flow Sheet I, but they obviously can also be used as described in Flow Sheet III to produce compounds with other bridging groups. Because of the extremely high potency of the tetrahydropyranones having a 6-(6-phenyl)phenyl group, these compounds, prepared as in Flow Sheet V, are especially to be preferred.

Flow Sheet VI shows an alternate preparation of the 6-phenyl substituted benzaldehydes IIIa. The imines formed between aniline and substituted benzaldehydes are treated with palladium (II) acetate to give stable complexes. These complexes are reacted with substituted phenyl Grignard reagents in the presence of triphenylphosphine to give, after acidic hydrolysis, the 6-phenyl substituted benzaldehydes IIIa.

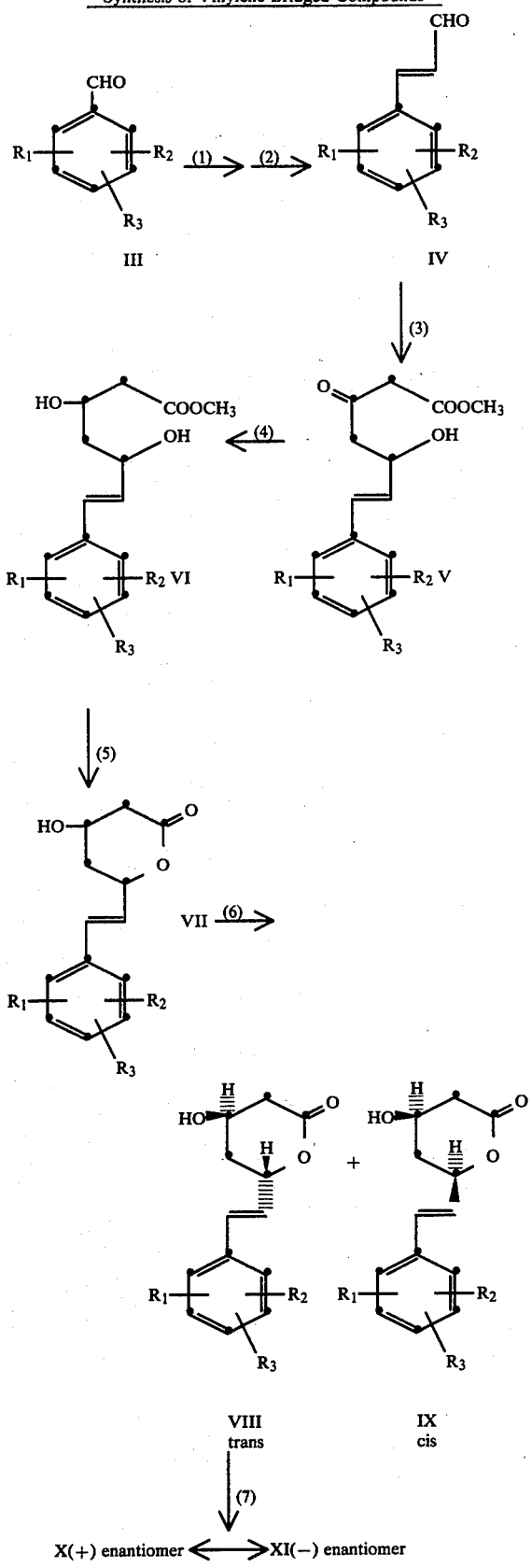

DEFINITIONS:

R₁, R₂ and R₃ are as defined in specifications for Formula I.

FLOW SHEET II
Preparation of Salts, Esters, Free Dihydroxy Acids

[Structure X] →(8)→ [Structure XII]

↓(11)   ↓(9)   ↘(10)

[Structure XIV] →(8)→ [Structure XIII] ←(9)

DEFINITIONS:

R₁, R₂ and R₃ are as defined in the specifications for Formula I

R₅ = $C_{1-5}$ lower alkyl or $C_{1-5}$ lower alkyl substituted by a phenyl, dimethylamino or acetamido group M⁺ = a pharmaceutically acceptable cation.

FLOW SHEET III
COMPOUNDS WITH OTHER BRIDGING GROUPS

A. Direct Bond from Phenyl Ring to Lactone Ring
[Procedure of Flow Sheet I omitting step (2)].

[Structure III] →(1)→(3)→ [Structure XV] →(4)→

-continued
FLOW SHEET III
COMPOUNDS WITH OTHER BRIDGING GROUPS

[Structure XVI]
↓(5)

[Structure XVIII] ←(7) trans racemate ←(6)— [Structure XVII]

XIX 4 (R) trans enantiomer    XVII

B. Methylene Bridge

[Structure XX] —(1)(3)(4)(5)(6)(7)→ [Structure XXI]

C. Ethylene Bridge

[Structure VIII] —(12)→ [Structure XXII]

D. Trimethylene Bridge

[Structure XXIII] —(32)→ [Structure XXIV]

↙(14)

-continued
FLOW SHEET III
COMPOUNDS WITH OTHER BRIDGING GROUPS

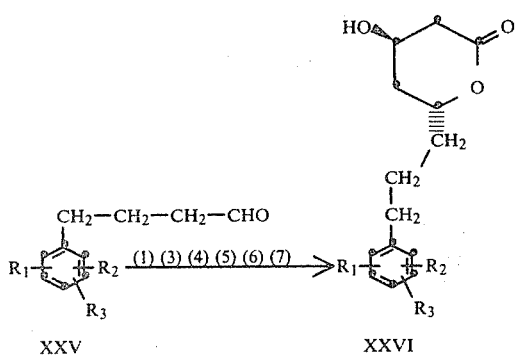

DEFINITIONS:

$R_1$, $R_2$ and $R_3$ are as defined in the specification for Formula I.

FLOW SHEET IV
SYNTHESIS OF SUBSTITUTED 4-HYDROXY-4-METHYL-3,4,5,6-TETRAHYDRO-2H-PYRAN-2-ONES

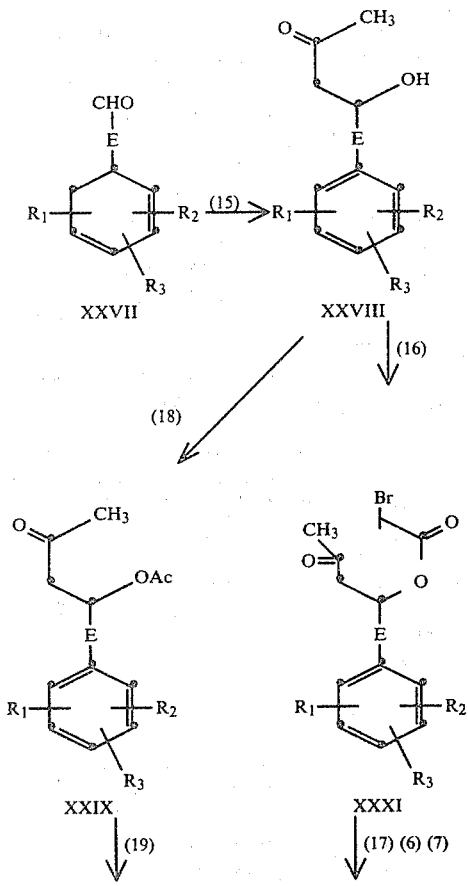

-continued
FLOW SHEET IV
SYNTHESIS OF SUBSTITUTED 4-HYDROXY-4-METHYL-3,4,5,6-TETRAHYDRO-2H-PYRAN-2-ONES

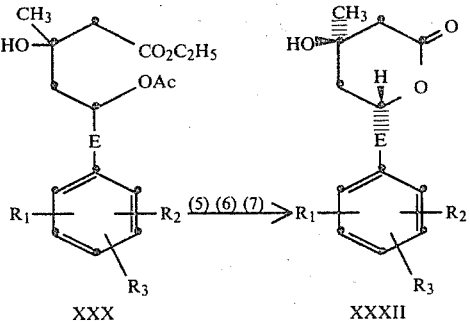

DEFINITIONS:

E, $R_1$, $R_2$ and $R_3$ are defined in the specifications given for Formula I.

FLOW SHEET V
SYNTHESIS OF 6-[2-[1,1'-biphenyl]-2-yl-ethenyl]pyranones

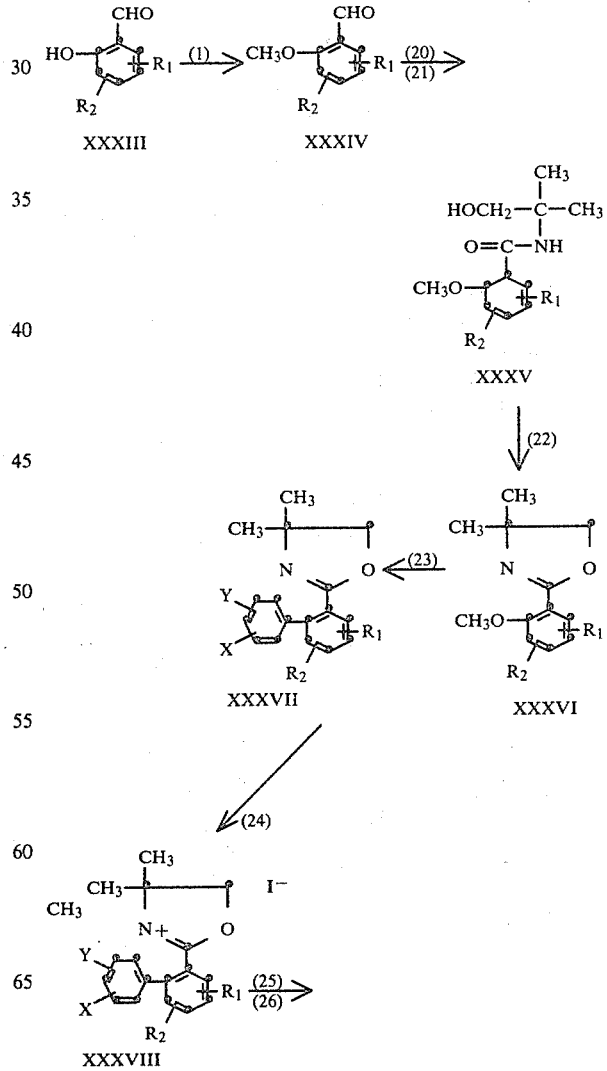

-continued
FLOW SHEET V
SYNTHESIS OF 6-[2-[1,1'-biphenyl]-2-yl-ethenyl]pyranones

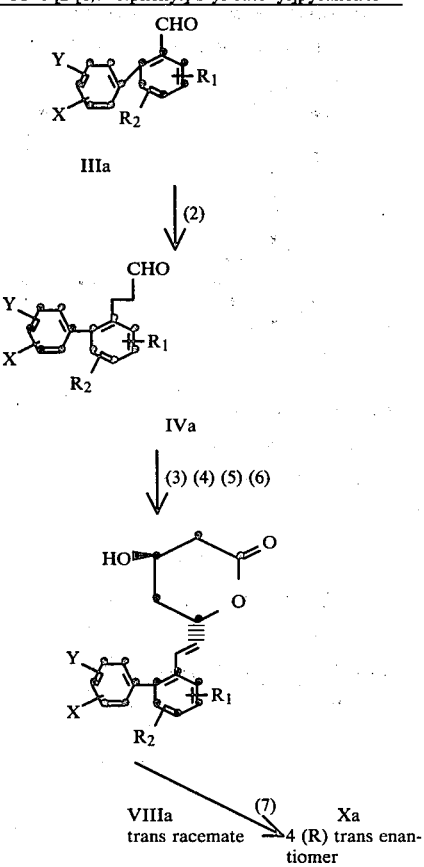

DEFINITIONS:

$R_1$ and $R_2$ are as defined in the specification for Formula I.

X and Y are halogen, $C_{1-4}$ alkyl or $C_{1-4}$ alkoxy.

III a, IV a, VIII a and X a are the special variants here of the general compounds in Flow Sheet I.

FLOW SHEET VI
ALTERNATE PREPARATION OF BENZALDEHYDES IIIa

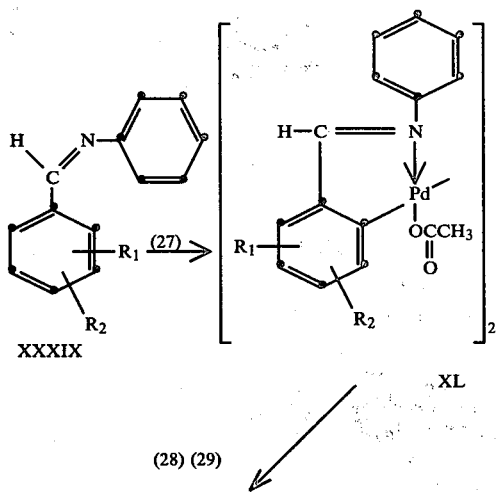

-continued
FLOW SHEET VI
ALTERNATE PREPARATION OF BENZALDEHYDES IIIa

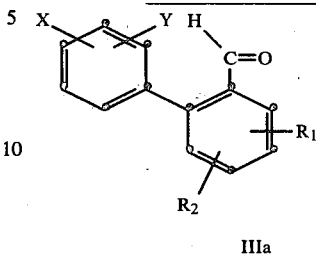

DEFINITIONS:

$R_1$ and $R_2$ are as defined in the specification for formula I.

X and Y are halogen, $C_{1-4}$ alkoxy or $C_{1-4}$ alkyl.

REACTIONS IN FLOW SHEETS I-VI

1. When $R_1$, $R_2$ or $R_3$ is HO— or bears a hydroxyl substituent, the HO— group is etherified using a reagent $R_4X$ in a suitable solvent such as DMF and the like in the presence of a suitable base, preferably an alkali metal carbonate such as $K_2CO_3$, to give the corresponding ether $R_4O$— which can be carried through the remainder of the synthesis. If it is desired to remove $R_4$ at a later synthetic step, $R_4$ is chosen as an easily removable group such as $CH_3OCH_2CH_2OCH_2$— (the MEM protecting group). The MEM group is removed readily by treatment with a Lewis acid catalyst such as $ZnBr_2$ in a suitable solvent such as $CH_2Cl_2$ and the like. When the starting material is devoid of a hydroxyl group, step (1) is omitted.

2. Aldol Reaction. This can be run in several ways:

(a) The classical Aldol synthesis in which acetaldehyde is condensed with the starting benzaldehyde, the resulting β-hydroxyaldehyde is acetylated with acetic anhydride and acetic acid is eliminated thermally to give the corresponding cinnamaldehyde.

(b) The directed Aldol condensation in which the anion of an appropriately N-substituted ethylidenylimine, such as ethylidenecyclohexylimine and the like, is condensed with the starting benzaldehyde at or below room temperature in an aprotic solvent, such as THF and the like, to afford a β-hydroxy-β-phenylpropylidenylimine which, upon concomitant dehydration and imine hydrolysis in an acidic medium, such as dilute aqueous HCl, provides the corresponding cinnamaldehyde.

(c) The use of a nucleophilic acetaldehyde equivalent in which cis-2-ethoxyvinyllithium, generated from cis-1-ethoxy-2-tri-n-butylstannylethylene, is condensed with the starting benzaldehyde to give an allylic alcohol which is subsequently rearranged, under suitable acidic conditions, to the corresponding cinnamaldehyde.

3. Dianion Step. Reaction with the dianion of acetoacetic ester in a suitable aprotic solvent such as THF, dioxane and the like.

4. Reduction with $NaBH_4$ in a suitable solvent such as methanol, ethanol and the like at or below room temperature.

5. Lactonization. Saponification by base (e.g. NaOH) in aqueous alcohol followed by acidification and cyclodehydration by heating in toluene. NOTE: Steps 3, 4 and 5 are usually carried out sequentially without purification of compounds V and VI.

6. Separation of the cis and trans racemic mixtures by chromatography on silica gel or crystallization.

7. Resolution of the trans racemate into its enantiomers by treating the (±)-trans lactone with either d-(+) or l-(−)-α-methylbenzylamine to give the diastereomeric dihydroxy amides which are separated by chromatography or crystallization. Hydrolysis of each pure diastereomeric amide under basic conditions, such as ethanolic NaOH and the like, affords the corresponding enantiomerically pure dihydroxy acid which, upon lactonization, e.g., in refluxing toluene, provides the pure (±)-trans or (−)-trans enantiomer. Stereochemistry depends on the absolute stereochemistry of the diastereomeric amide from which it is derived.

8. Saponification with M+ −OH where M+ is an alkali metal cation.

9. Careful acidification.

10. Mild hydrolysis

11. Nucleophilic opening of the lactone ring with an alcohol, R₅OH, in the presence either of a basic catalyst, particularly the corresponding alkoxide, R₅O−, or an acidic catalyst such as an acidic ion exchange resin, e.g. Amberlite 120.

12. Hydrogenation in the presence of a suitable catalyst such as Rhodium or Palladium on carbon.

13. Reaction with NaCN in a suitable solvent such as aqueous ethanol and the like.

14. Reduction with DIBAL in an aprotic solvent such as toluene, ether and the like followed by work up with an aqueous acid such as 5% H₂SO₄.

15. Aldol condensation with 1-(tri-n-butyl stannyl)-propan-2-one.

16. Acylation with 2-bromoacetyl bromide.

17. Intramolecular Reformatsky reaction carried out, for example, in the presence of activated zinc dust, cuprous bromide and diethylaluminum chloride.

18. Acylation with acetyl chloride.

19. Intermolecular Reformatsky reaction carried out with ethyl 2-bromacetate, for example, in the presence of the reagents indicated in step (17) above.

20. Treatment with N-bromosuccinimide in CCl₄ with irradiation by a sun lamp (*Tetrahedron Letters*, 3809 (1979)).

21. Treatment with two equivalents of the amine $$H_2N-\underset{\underset{CH_3}{|}}{\overset{\overset{CH_3}{|}}{C}}-CH_2OH$$

22. Reaction with SOCl₂ (*J. Org. Chem.*, 43, 1372 (1978)).

23. Reaction with a substituted phenyl Grignard reagent

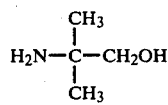

24. Reaction with methyl iodide in a suitable solvent such as acetone.

25. Reaction with NaBH₄ in a suitable solvent such as ethanol or methanol.

26. Heating with acid (*J. Het. Chem.*, 3, 531 (1966)).

27. Reaction with Palladium (II) acetate in acetic acid at reflux.

28. Reaction with a substituted Grignard reagent

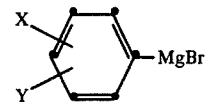

in suitable solvents such as benzene or toluene in the presence of triphenylphosphine.

29. Hydrolysis with 6 N HCl at ambient temperature.

A further aspect of the present invention is a pharmaceutical composition consisting of at least one of the compounds of formula I in association with a pharmaceutical vehicle or diluent. The pharmaceutical composition can be formulated in a classical manner utilizing solid or liquid vehicles or diluents and pharmaceutical additives of a type appropriate to the mode of desired administration. The compounds can be administered by an oral route, for example, in the form of tablets, capsules, granules or powders, or they can be administered by a parenteral route in the form of injectable preparations. The dose to be administered depends on the unitary dose, the symptoms, and the age and the body weight of the patient. A dose for adults is preferably between 200 and 2,000 mg per day, which can be administered in a single dose or in the form of individual doses from 1–4 times per day.

A typical capsule for oral administration contains active ingredient (250 mg), lactose (75 mg) and magnesium stearate (15 mg). The mixture is passed through a 60 mesh sieve and packed into a No. 1 gelatin capsule.

A typical injectable preparation is produced by asceptically placing 250 mg of sterile active ingredient into a vial, asceptically freeze-drying and sealing. For use, the contents of the vial are mixed with 2 ml of physiological saline, to produce an injectable preparation.

The compounds of this invention also have useful antifungal activities. For example, they may be used to control strains of *Penicillium sp., Aspergillus niger, Cladosporium sp., Cochliobolus miyabeorus* and *Hilminthosporium cynodnotis*. For those utilities they are admixed with suitable formulating agents, powders, emulsifying agents or solvents such as aqueous ethanol and sprayed or dusted on the plants to be protected.

This invention can be illustrated by the following examples in which ratios of solvents are in volumes and percentages, unless otherwise indicated, or by weight.

EXAMPLE 1

Preparation of (E)-6-[2-(2,4-Dichloro-6-(phenylmethoxy)phenyl)ethenyl]-3,4,5,6-tetrahydro-4-hydroxy-2H-pyran-2-one Step A. Preparation of 2,4-Dichloro-6-phenylmethoxybenzaldehyde Potassium carbonate (9.4 g, 67.8 mmole) was added to a stirred solution of 4,6-dichlorosalicylaldehyde (10.8 g, 56.5 mmole) in dimethylformamide (80 ml). The resulting mixture was stirred at 60° for 30 minutes and treated with benzyl bromide (10.6 g, 62.1 mmole). This mixture was stirred one hour at 60° C. and then poured into ice water (1000 ml) to give the title compound (15.9 g, 100%) which melted at 98°–100° C. after recrystallization from hexane. pmr (CDCl₃) δ5.10 (2H, s), 7.33 (5H, s), 10.40 (H, s).

Analysis Calc. for C₁₄H₁₀Cl₂O₂: Calc.: C, 59.81; H, 3.58; Found: C, 59.98; H, 3.58.

Step B. Preparation of (E)-2,4-Dichloro-6-phenylmethoxycinnamaldehyde

A stirred suspension of 2,4-dichloro-6-phenylmethoxybenzaldehyde (15.5 g, 55.1 mmole) in acetaldehyde (30 ml) was cooled to 5° C. and treated with 25% methanolic potassium hydroxide (1.4 ml, 6.24 mmole) at such a rate that the internal temperature was maintained at 25°–30° C. The resulting solution was stirred for 30 minutes in the ice bath, treated with acetic anhydride (30 ml) and then heated at 100° C. for 30 minutes. After cooling to 30° C. the solution was treated with water (84 ml) and 12 N hydrochloric acid (7 ml). The resulting mixture was refluxed for 30 minutes and then cooled in an ice bath to give a gummy solid which was recrystallized from cyclohexane to give the title compound (5.6 g, 33%), mp 109°–112° C.: pmr (CDCl$_3$) δ5.10 (2H, s), 7.33 (5H, s), 9.68 (H, d).

Analysis Calc. for $C_{16}H_{12}Cl_2O_2$: Calc.: C, 62.56; H, 3.94 Found: C, 62.66; H, 3.98.

Alternate Step B. Preparation of (E)-2,4-Dichloro-6-phenylmethoxycinnamaldehyde A 1.6 M solution (18.8 ml, 30 mmole) of n-butyllithium in hexane was added cautiously to a stirred solution of freshly distilled diisopropylamine (3.0 g, 30 mmole) in anhydrous tetrahydrofuran (200 ml) maintained at 0° C. under a nitrogen atmosphere. The resulting solution was stirred at 0° C. for 15 minutes and then treated with ethylidenecyclohexylamine (3.75 g, 30 mmole). The solution was stirred 15 minutes at 0° C., cooled to −78° C. and treated with a solution of 2,4-dichloro-6-phenylmethoxybenzaldehyde (8.4 g, 30 mmole) in anhydrous tetrahydrofuran (50 ml). The resulting red solution was stirred at −78° C. for 15 minutes and then at 25° C. for 60 minutes. The reaction solution was treated with water (200 ml) and extracted with ether (3×200 ml). The organic extracts were combined, washed with brine (3×100 ml), dried over magnesium sulfate and filtered. The filtrate was evaporated in vacuo, leaving the desired intermediate hydroxyimine as a brown viscous oil (12.5 g): pmr (CDCl$_3$) δ5.10 (2H, s), 5.50 (H, t), 7.37 (5H, s), 7.70 (H, s).

A solution of the oily imine (12.5 g) in tetrahydrofuran (110 ml) was treated with a solution of oxalic acid dihydrate (11 g, 87.2 mmole) in water (22 ml). The resulting solution was refluxed for 30 minutes, cooled to 25° C. and poured into water (500 ml). The resulting mixture was extracted with ether (3×200 ml). The organic extracts were combined, washed with brine (3×50 ml), dried over magnesium sulfate and filtered. The filtrate was evaporated in vacuo, leaving the title compound as a tan solid. The title compound was purified by recrystallization from cyclohexane to give yellow needles (4.7 g, 51%) melting at 109°–111° C.: pmr (CDCl$_3$) δ5.11 (2H, s), 7.33 (5H, s), 9.68 (H, d).

Alternate to Alternate Step B. Preparation of (E)-2,4-Dichloro-6-phenylmethoxycinnamaldehyde A 1.37 M solution (24.1 ml, 33 mmole) of n-butyllithium in hexane was added cautiously to a stirred solution of cis-1-ethoxy-2-tri-n-butylstannylethylene (11.9 g, 33 mmole) in anhydrous tetrahydrofuran (75 ml) maintained at −78° C. under a nitrogen atmosphere. The resulting solution was stirred at −78° C. for one hour and then treated with a solution of 2,4-dichloro-6-phenylmethoxybenzaldehyde (8.4 g, 30 mmole) in anhydrous tetrahydrofuran (50 ml). The resulting brown solution was stirred at −78° C. for one hour and then allowed to warm to 20° C. The reaction solution was quenched with saturated aqueous sodium bicarbonate (25 ml), diluted with water (100 ml) and then extracted with ether (2×200 ml). The organic extracts were combined, washed with brine (2×100 ml), dried over magnesium sulfate and filtered. The filtrate was evaporated in vacuo, leaving the desired intermediate allylic alcohol as a yellow oil.

The oil was chromatographed on a silica column (400 g) to cause allylic rearrangement to the desired product. Elution with methylene chloride (200 ml) provided a forerun containing tetrabutyltin which was discarded. Continued elution with methylene chloride/methanol (98:2, v:v; 1500 ml) gave the title compound as a pale yellow solid, mp 109°–111° C. (6.4 g, 70%).

Step C. Preparation of Methyl (E)-7-(2,4-dichloro-6-phenylmethoxyphenyl)-5-hydroxy-3-oxo-6-heptenoate Methyl acetoacetate (9.56 g, 82.3 mmole) was added dropwise to a stirred suspension of sodium hydride (50% oil suspension) (3.95 g, 82.3 mmole) in anhydrous tetrahydrofuran at 0° C. under a nitrogen atmosphere. The resulting solution was stirred 15 minutes at 0° C. and then treated with a 1.6 M solution (51.5 ml, 82.3 mmole) of n-butyllithium in hexane over 5 minutes. The resulting yellow solution was stirred 15 minutes at 0° C. and then treated with a solution of (E)-2,4-dichloro-6-phenylmethoxycinnamaldehyde (25.3 g, 82.3 mmole) in anhydrous tetrahydrofuran (150 ml). The resulting orange solution was stirred 15 minutes at 0° C. and then quenched by dropwise addition of 12 N hydrochloric acid (ca. 20 ml). The reaction mixture was diluted with water (100 ml) and extracted with ether (3×300 ml). The organic extracts were combined, washed with brine (3×100 ml), dried over magnesium sulfate and filtered. The filtrate was evaporated in vacuo leaving the title compound as a yellow oil (34.8 g, 100%): pmr (CDCl$_3$) δ2.75 (2H, d), 3.45 (2H, s), 3.72 (3H, s), 4.71 (H, m), 5.50 (2H, s), 7.37 (5H, s).

Step D. Preparation of Methyl (E)-7-(2,4-Dichloro-6-phenylmethoxyphenyl)-3,5-dihydroxy-6-heptenoate Sodium tetrahydridoborate (1.55 g, 41.1 mmole) was added with stirring to a cooled solution (5° C.) of methyl (E)-7-(2,4-dichloro-6-phenylmethoxyphenyl)-5-hydroxy-3-oxo-6-heptenoate (34.8 g, 82.3 mmole) in ethanol (200 ml) at a rate sufficient to maintain the internal temperature at 15°–20° C. The resulting solution was stirred with ice-bath cooling for 15 min. and then acidified with 6 N hydrochloric acid. The resulting mixture was diluted with water (500 ml) and extracted with ether (3×250 ml). The organic extracts were combined, washed with brine (4×100 ml), dried over magnesium sulfate and filtered. The filtrate was evaporated in vacuo, leaving the title compound as a yellow oil (34.8 g, 99.5%): pmr CDCl$_3$) δ2.45 (2H, d), 3.65 (3H, s), 4.18 (H, m), 4.45 (H, m), 4.98 (2H, s), 7.28 (5H, s).

Step E. Preparation of (E)-7-(2,4-Dichloro-6-phenylmethoxyphenyl)-3,5-dihydroxy-6-heptenoic acid A solution of methyl (E)-7-(2,4-dichloro-6-phenylmethoxyphenyl)-3,5-dihydroxy-6-heptenoate (34.8 g, 81.8 mmole), 1 N sodium hydroxide (82 ml, 82 mmole) and ethanol (200 ml) was stirred at 25° C. for 15 min. The reaction solution was acidified with 6 N hydrochloric acid, diluted with water (400 ml) and extracted with ether (3×200 ml). The combined organic extracts were washed with brine (3×100 ml), dried over magnesium sulfate and filtered. The filtrate was evaporated in vacuo, leaving the title compound as an orange oil (33.3 g, 99%): pmr (CDCl$_3$) δ2.47 (2H, d), 4.30 (2H, br m), 4.98 (2H, s), 7.30 (5H, s).

Step F. Preparation of (E)-6-[2-(2,4-Dichloro-6-phenylmethoxyphenyl)ethenyl]-3,4,5,6-tetrahydro-4-hydroxy-2H-pyran-2-one A solution of (E)-7-(2,4-dichlorophenylmethoxyphenyl)-3,5-dihydroxy-6-heptenoic acid (33.3 g, 81.3 mmole) in toluene (300 ml) was heated at reflux in a Dean-Stark apparatus. After 2 hours the Dean-Stark apparatus was replaced with a soxhlet containing 3A molecular sieves (100 g). The solution was refluxed for an additional 4 hours and then the toluene was removed in vacuo leaving a yellow oil (31.7 g) which is a mixture of cis and trans isomers of the title compound. The oil was chromatographed on a silica gel column (900 g). Elution with methylene chloride-acetone (9:1, v:v; 4000 ml) provided a forerun which was discarded. Continued elution with the same eluant (500 ml) gave the trans isomer of the title compound as a pale yellow solid (5.8 g).

Further elution of the column with the same eluant (3250 ml) gave a tan solid (8.8 g), which is a mixture of the cis and trans isomers of the title compound. This cis/trans mixture was chromatographed using a Waters Prep LC500. Separation of this mixture was accomplished by using two prep PAK-500/silica cartridges in series and eluting with methylene chloride-acetone (9:1, v:v). Using the shave recycle technique, the cis (4.7 g) and the trans (3.3 g) isomers of the title compound were obtained. The fractions of the trans isomer, collected from the two chromatographys, were combined and recrystallized from n-butyl chloride to give the trans isomer of the title compound (7.3 g, 23%), mp 130°–131° C.: pmr (CDCl$_3$) δ2.64 (2H, m), 4.30 (H, m), 5.07 (2H, s), 5.30 (H, m), 7.42 (5H, s).

Analysis Calc. for C$_{20}$H$_{18}$Cl$_2$O$_4$: Calc.: C, 61.08; H, 4.61; Found: C, 61.12; H, 4.60.

The cis isomer (4.3 g, 13%) of the title compound melted at 130°–131.5° C. after recrystallization from n-butyl chloride: pmr (CDCl$_3$) δ4.30 (H, m), 4.83 (H, m), 5.12 (2H, s), 7.47 (5H, s).

Analysis Calc. for C$_{20}$H$_{18}$Cl$_2$O$_4$: Calc.: C, 61.08; H, 4.61; Found: C, 61.55; H, 4.63.

EXAMPLE 2

Starting with 4,6-dichlorosalicylaldehyde but substituting equimolar amounts of the following alkyl halide or tosylate in place of benzyl bromide in Step A of Example 1 and following the procedure of Steps A through F there was obtained a corresponding amount of the appropriate end product listed below.

| Alkyl Halide or Tosylate | End Product | Isomer | M.P. °C. | | Calc. | Fd. |
|---|---|---|---|---|---|---|
| n-pentyl iodide | (E)-6-[2-(2,4-dichloro-6-n-pentyloxyphenyl)ethenyl]-3,4,5,6-tetrahydro-4-hydroxy-2H-pyran-2-one | trans | 81–83 | C | 57.92 | 57.68 |
| | | | | H | 5.94 | 6.01 |
| | | cis | oil | C | 57.92 | 57.54 |
| | | | | H | 5.94 | 6.09 |
| 3,4-dichlorobenzyl chloride | (E)-6-{2-[2,4-dichloro-6-(3,4-dichlorophenylmethoxy)phenyl]ethenyl}-3,4,5,6-tetrahydro-4-hydroxy-2H-pyran-2-one | trans | 73–75 | C | 52.27 | 52.03 |
| | | | | H | 3.73 | 3.74 |
| diphenylmethyl bromide | (E)-6-[2-(2,4-dichloro-6-diphenylmethoxyphenyl)ethenyl]3,4,5,6-tetrahydro-4-hydroxy-2H-pyran-2-one | trans | 135.5–137 | C | 66.53 | 66.71 |
| | | | | H | 4.72 | 4.63 |
| allyl bromide | (E)-6-[2-(2,4-dichloro-6-allyloxyphenyl)ethenyl]-3,4,5,6-tetrahydro-4-hydroxy-2H-pyran-2-one | trans | 82–84 | C | 55.99 | 56.14 |
| | | | | H | 4.70 | 4.70 |
| 2-methoxyethoxymethyl chloride | (E)-6-{2-[2,4-dichloro-6-(2-methoxyethoxymethoxy)phenyl]ethenyl}',4,5,6-tetrahydro-4-hydroxy-2H-pyran-2-one | trans | oil | C | 52.19 | 52.04 |
| | | | | H | 5.15 | 5.05 |
| methylthiomethyl chloride | (E)-6-[2-(2,4-dichloro-6-methylthiomethoxyphenyl)ethenyl]-3,4,5,6-tetrahydro-4-hydroxy-2H-pyran-2-one | trans | oil | C | 49.60 | 49.97 |
| | | | | H | 4.44 | 4.74 |
| 2-(adamant-1-yl)ethyl toluene-p-sulphonate | (E)-6-{2-[2,4-dichloro-6-(2-adamant-1-ylethoxy)phenyl]ethenyl}-3,4,5,6-tetrahydro-4-hydroxy-2H-pyran-2-one | trans | 174–6 | C | 64.52 | 64.38 |
| | | | | H | 6.52 | 6.70 |
| 4-chlorobenzyl bromide | (E)-6-{2-[6-(4-chlorophenylmethoxy-2,4-dichlorophenyl]ethenyl}-3,4,5,6-tetrahydro-4-hydroxy-2H-pyran-2-one | trans | 111.5–113 | C | 56.16 | 56.08 |
| | | | | H | 4.01 | 3.98 |
| 1-bromo-3-phenylpropane | (E)-6-{2-[2,4-dichloro-6-(3-phenylpropoxy)phenyl]ethenyl}-3,4,5,6-tetrahydro-4-hydroxy-2H-pyran-2-one | trans | 93–94 | C | 62.71 | 62.66 |
| | | | | H | 5.26 | 5.25 |
| 1-bromo-2- | (E)-6-[2-(2,4-dichloro-6- | trans | 125– | C | 61.93 | 62.18 |

-continued

| Alkyl Halide or Tosylate | End Product | Isomer | M.P. °C. | | Calc. | Fd. |
|---|---|---|---|---|---|---|
| phenylethane | phenylethoxyphenyl)ethenyl]-3,4,5,6-tetrahydro-4-hydroxy-2H-pyran-2-one | | 126 | H | 4.95 | 5.07 |
| cinnamyl bromide | (E) (E)-6-{2-[2,4-dichloro-6-(3-phenyl-2-propenyloxy)-phenyl]ethenyl}-3,4,5,6-tetrahydro-4-hydroxy-2H-pyran-2-one | trans | 120–122 | C H | 63.02 4.81 | 62.73 4.81 |
| 1-bromo-3,5,5-trimethylhexane | (E)-6-{2-[2,4-dichloro-6-(3,5,5-trimethylhexyloxy)phenyl]ethenyl}-3,4,5,6-tetrahydro-4-hydroxy-2H-pyran-2-one | trans | 53–66 | C H | 61.54 7.04 | 61.60 7.27 |
| 4-methylbenzyl bromide | (E)-6-{2-[2,4-dichloro-6-(4-methylphenylmethoxy)phenyl]ethenyl}-3,4,5,6-tetrahydro-4-hydroxy-2H-pyran-2-one | trans | 113–118 | C H | 61.92 4.95 | 62.05 5.05 |
| 4-methoxybenzyl bromide | (E)-6-{2-[2,4-dichloro-6-(4-methoxyphenyl methoxy)phenyl]ethenyl}-3,4,5,6-tetrahydro-4-hydroxy-2H-pyran-2-one | trans | 114–115 | C H | 59.58 4.76 | 59.73 4.75 |
| 4-fluorobenzyl bromide | (E)-6-{2-[2,4-dichloro-6-(4-fluorophenylmethoxy)phenyl]ethenyl}-3,4,5,6-tetrahydro-4-hydroxy-2H-pyran-2-one | trans | 124–6 | C H | 58.41 4.17 | 58.26 4.20 |
| | | cis | 131–3 | C H | 58.41 4.17 | 58.29 4.06 |
| 2-fluorobenzyl chloride | (E)-6-{2-[2,4-dichloro-6-(2-fluorophenylmethoxy-phenyl]ethenyl}-3,4,5,6-tetrahydro-4-hydroxy-2H-pyran-2-one | trans | 140–141.5 | C H | 58.41 4.17 | 58.43 4.20 |
| 2,4-diflurobenzyl bromide | (E)-6-{2-[2,4-dichloro-6-(2,4-difluorophenylmethoxy)phenyl]ethenyl}-3,4,5,6-tetrahydro-4-hydroxy-2H-pyran-2-one | trans | 138–139 | C H | 55.96 3.76 | 56.00 3.82 |
| 3-fluorobenzyl bromide | (E)-5-{2-[2,4-dichloro-6(3-fluorophenylmethoxy)-phenyl]ethenyl}3,4,5,6-tetrahydro-4-hydroxy-2H-pyran-2-one | trans | 91.5–92 | C H | 58.41 4.17 | 58.48 4.22 |
| 2,3,4,5,6-pentafluorobenzyl chloride | (E)-6-{2-[2,4-dichloro-6-(2,3,4,5,6-pentafluorophenylmethoxy)phenyl]-ethenyl}-3,4,5,6-tetrahydro-4-hydroxy-2H-pyran-2-one. 0.5 chlorobutane | trans | 72–75 | C H | 49.90 3.33 | 49.87 3.35 |

EXAMPLE 3

By substituting an equimolar amount of 3,5-dichlorosalicylaldehyde for 4,6-dichlorosalicylaldehyde and an equimolar amount of n-pentyl iodide for benzyl bromide in Step A of Example 1 and following the procedure for Steps A through F, there was obtained a corresponding amount of the following end product.

(E)-6-[2-(3,5-Dichloro-2-pentyloxyphenyl)ethenyl]-3,4,5,6-tetrahydro-4-hydroxy-2H-pyran-2-one, trans isomer: yellow oil.

Analysis calc for $C_{18}H_{22}Cl_2O_4$: Calc.: C, 57.92; H, 5.94; Found: C, 57.83; H, 5.91 cis isomer: yellow oil.

Analysis calc. for $C_{18}H_{22}Cl_2O_4$: Calc.: C, 57.92; H, 5.94; Found: C, 57.54; H, 6.09.

EXAMPLE 4

By substituting an equimolar amount of the following aldehydes in place of 2,4-dichloro-6-phenylmethoxybenzaldehyde in Step B of Example 1 and then following the procedures of Steps B through F, there was obtained a corresponding amount of the appropriate end product listed below.

| Aldehyde | End Product | Isomer | M.P. °C. | | Calc. | Fd. |
|---|---|---|---|---|---|---|
| 2,4-dichlorobenzaldehyde | (E)-6-[2-(2,4-dichlorophenyl)ethenyl]-3,4,5,6-tetrahydro-4-hydroxy-2H-pyran-2-one | trans | 146–148 | C H | 54.37 4.21 | 54.57 4.31 |
| | | cis | 115–117 | C H | 54.37 4.21 | 54.24 3.96 |
| 2,4-dimethylbenzaldehyde | (E)-6-[2-(2,4-dimethylphenyl)ethenyl]-3,4,5,6-tetrahydro-4-hydroxy-2H-pyran-2-one | trans | 111–113 | C H | 73.14 7.36 | 73.07 7.46 |
| | | cis | 110–112 | C H | 73.14 7.36 | 72.77 7.57 |

-continued

| Aldehyde | End Product | Isomer | M.P. °C. | | Calc. | Fd. |
|---|---|---|---|---|---|---|
| 2,6-dichloro-benzaldehyde | (E)-6-[2-(2,4-dichloro-phenyl)ethenyl]-3,4,5,6-tetrahydro-4-hydroxy-2H-pyran-2-one | trans | 102–104 | C<br>H | 54.37<br>4.21 | 54.65<br>4.21 |
| | | cis | 118–119 | C<br>H | 54.37<br>4.21 | 54.37<br>4.17 |
| 2-chloro-benzaldehyde | (E)-6-[2-(2-chlorophenyl)-ethenyl]-3,4,5,6-tetrahydro-4-hydroxy-2H-pyran-2-one | trans | 129–131 | C<br>H | 61.79<br>5.18 | 61.89<br>5.38 |
| 4-phenyl-benzaldehyde | (E)-6-[2-(4-biphenyl)-ethenyl]-3,4,5,6-tetrahydro-4-hydroxy-2H-pyran-2-one | trans | 148–150 | C<br>H | 77.53<br>6.16 | 77.74<br>6.02 |

EXAMPLE 5

By substituting an equimolar amount of the following aldehydes for (E)-2,4-dichloro-6-phenylmethoxycinnamaldehyde in Step C of Example 1 and following the procedure for Steps C through F, there was obtained a corresponding amount of the appropriate end product listed below.

| Aldehyde | End Product | Isomer | M.P. °C. | | Calc. | Fd. |
|---|---|---|---|---|---|---|
| benzaldehyde | 3,4,5,6-tetrahydro-4-hydroxy-6-phenyl-2H-pyran-2-one | trans | 91–93 | C<br>H | 68.73<br>6.29 | 68.56<br>6.49 |
| benzaldehyde | 3,4,5,6-tetrahydro-4-hydroxy-6-phenyl-2H-pyran-2-one | cis | 91–93 | C<br>H | 68.73<br>6.29 | 68.72<br>6.41 |
| (E)-cinnamaldehyde | (E)-3,4,5,6-tetrahydro-4-hydroxy-6-(2-phenylethenyl)-2H-pyran-2-one | trans | 96–98.5 | C<br>H | 71.54<br>6.46 | 71.41<br>6.59 |
| (E)-cinnamaldehyde | (E)-3,4,5,6-tetrahydro-4-hydroxy-6-(2-phenylethenyl)-2H-pyran-2-one | cis | 91–92.5 | C<br>H | 71.54<br>6.46 | 71.79<br>6.53 |
| 4-phenylbenz-aldehyde | 6-(4-biphenyl)-3,4,5,6-tetrahydro-4-hydroxy-2H-pyran-2-one | trans | 135–137 | C<br>H | 76.10<br>6.01 | 76.28<br>5.68 |
| 4-phenylbenz-aldehyde | 6-(4-biphenyl)-3,4,5,6-tetrahydro-4-hydroxy-2H-pyran-2-one | cis | 146–148 | C<br>H | 76.10<br>6.01 | 76.11<br>5.67 |
| 2,4-dichloro-benzaldehyde | 6-(2,4-dichlorophenyl)-3,4,5,6-tetrahydro-4-hydroxy-2H-pyran-2-one | trans | 133–136 | C<br>H | 50.60<br>3.86 | 50.88<br>3.87 |
| 2,4-dichloro-phenoxyacet-aldehyde | 6-(2,4-dichlorophenoxy-methyl)-3,4,5,6-tetrahydro-4-hydroxy-2H-pyran-2-one | trans | "oil" | C<br>H | 49.51<br>4.15 | 49.24<br>4.10 |

EXAMPLE 6

Preparation of (E)-6-[2-(2,3-Dichlorophenyl)ethenyl]-3,4,5,6-tetrahydro-4-hydroxy-2H-pyran-2-one Step A. Preparation of (E)-2,3-Dichlorocinnamaldehyde Anhydrous aluminum chloride (10.5 g, 78.8 mmole) was slowly added to a stirred solution of 2,3-dichloro-benzoyl chloride (14.4 g, 68.7 mmole) and bis-trimethyl-silylacetylene (12.8 g, 75.1 mmole) in dry methylene chloride maintained at 0° C. The dark brown reaction mixture was stirred 5 minutes at 0° C. and 2 hours at 25° C. and then poured into ice water. The organic product was extracted into ether (4×200 ml). The ether extracts were combined, washed with brine (3×100 ml), dried over magnesium sulfate and filtered. The filtrate was evaporated in vacuo leaving the desired intermediate trimethylsilylacetylenic ketone as a brown oil (18.4 g, 98%), pmr (CDCl$_3$) δ0.30 (9H, s), 7.47 (3H, m).

Sodium methoxide (0.81 g, 15.0 mmole) was added to a stirred solution of the oily trimethylsilylacetylenic ketone (18.4 g, 67.8 mmole) in methanol (200 ml) maintained at 0° C. in an ice bath. After 5 minutes the ice bath was removed and the reaction solution was stirred 30 minutes at 25° C. The resulting solution was cooled to 0° C. and sodium tetrahydridoborate (0.9 g, 23.8 mmole) was slowly added. This reaction solution was stirred 30 minutes at 25° C. and then poured into ice water. The organic product was extracted into ether (4×150 ml). The ether extracts were combined, washed with brine (3×100 ml), dried over magnesium sulfate and filtered. The filtrate was evaporated in vacuo, leaving the desired β-hydroxydimethylacetal as a brown oil. Hydrochloric acid (6 N, 50 ml) was added to the solution of the crude β-hydroxydimethylacetal in dioxane (100 ml). The resulting mixture was heated on the steam bath for 30 minutes, and then poured into ice water (1000 ml) to give the title compound as a brown solid (12.7 g). This solid was chromatographed on a silica gel column (700 g). Elution with ethyl acetate-hexane (2:8, V:V; 1250 ml) provided a forerun which was discarded. Continued elution with the same eluant (1125 ml) gave the title compound (10.6 g, 78%) which melted at 94°–95° C.: pmr (CDCl$_3$) δ6.70 (H, dd), 7.98 (H, d), 9.86 (H, d).

Analysis Calc. for $C_9H_6Cl_2O$: Calc.: C, 53.76; H, 3.01 Found: C, 53.52; H, 2.86

Step B. Preparation of (E)-6-[2-(2,3-Dichlorophenyl)ethenyl]-3,4,5,6-tetrahydro-4-hydroxy-2H-pyran-2-one By substituting an equimolar amount of (E)-2,3-dichlorocinnamaldehyde for (E)-2,4-dichloro-6-phenylmethoxycinnamaldehyde in Step C of Example 1 and following the procedure for Steps C through F, there was obtained a corresponding amount of the title compound.

trans isomer: mp 122°–123° C.

Analysis Calc. for $C_{13}H_{12}Cl_2O_3$: Calc.: C, 54.37; H, 4.21; Found: C, 54.31; H, 4.25.

cis isomer: mp 131°–132° C.

Analysis Calc. for $C_{13}H_{12}Cl_2O_3$: Calc. C, 54.37; H, 4.21; Found: C, 54.52; H, 4.25.

EXAMPLE 7

Preparation of (E)-6-[2-([1,1'-Biphenyl]-2-yl)ethenyl]-3,4,5,6-tetrahydro-4-hydroxy-2H-pyran-2-one By substituting an equimolar amount of [1,1'-biphenyl]-2-carbonyl chloride for 2,3-dichlorobenzoyl chloride in Step A of Example 6 and following the procedure for Steps A and B, there was obtained a corresponding amount of the title compound.

trans isomer: mp 89°–91° C.

Analysis Calc. for $C_{19}H_{18}O_3$: Calc.: C, 77.53; H, 6.16; Found: C, 77.51; H, 6.17.

cis isomer: yellow glass

Analysis Calc. for $C_{19}H_{18}O_3$; Calc.: C, 77.53; H, 6.16; Found: C, 77.26; H, 6.07.

EXAMPLE 8

Preparation of Trans-6-[2-(2,4-Dichloro-6-phenylmethoxyphenyl)ethyl]-3,4,5,6-tetrahydro-4-hydroxy-2H-pyran-2-one A solution of trans-(E)-6-[2-(2,4-dichloro-6-phenylmethoxyphenyl)ethenyl]-3,4,5,6-tetrahydro-4-hydroxy-2H-pyran-2-one (1.1 g, 28 mmole) in tetrahydrofuran (50 ml) was magnetically stirred and hydrogenated at room temperature and atmospheric pressure in the presence of 110 mg of 5% rhodium on carbon catalyst until 1.5 molar equivalents of hydrogen had been consumed. After removing the catalyst by filtration, the filtrate was evaporated in vacuo leaving the title compound as a pale yellow oil. The oil was chromatographed on a silica gel column (200 g). Elution with acetone-methylene chloride (1:9, v:v; 560 ml) provided a forerun which was discarded. Continued elution with the same eluant (240 ml) gave the title compound as a colorless oil which solidified when it was triturated with ether. The title compound was purified by recrystallization from ether-hexane (1:1, v:v; 20 ml) to give colorless needles (0.67 g, 61%) melting at 99°–101° C.: pmr (CDCl$_3$) δ1.83 (4H, m), 2.60 (2H, m), 2.90 (2H, m), 4.30 (H, m), 4.62 (H, m), 5.05 (2H, s), 7.42 (5H, s).

Analysis Calc. for $C_{20}H_{20}Cl_2O_4$: Calc.: C, 60.77; H, 5.10; Found: C, 60.96; H, 4.85.

EXAMPLE 9

By substituting an equimolar amount of the following 2H-pyran-2-ones for trans-(E)-6-[2-(2,4-dichloro-6-phenylmethoxyphenyl)ethenyl]-3,4,5,6-tetrahydro-4-hydroxy-2H-pyran-2-one in Example 8 and following the procedure of Example 8, there was obtained a corresponding amount of the following end products.

| 2H-Pyran-2-one | End Product | M.P. °C. | | Calc. | Fd. |
|---|---|---|---|---|---|
| trans-(E)-6-(2-phenylethenyl)-3,4,5,6-tetrahydro-4-hydroxy | trans-6-(2-phenylethyl)-3,4-5,6-tetrahydro-4-hydroxy-2H-pyran-2-one | 76–77 | C H | 70.88 7.32 | 71.02 7.41 |
| trans-(E)-6-[2-(2,4-dichlorophenyl)-ethenyl]-3,4,5,6-tetrahydro-4-hydroxy | trans-6-[2-(2,4-dichlorophenyl)-ethyl]-3,4,5,6-tetrahydro-4-hydroxy-2H-pyran-2-one | 95–97 | C H | 54.00 4.88 | 53.80 4.71 |
| cis-(E)-6-[2-(2,4-dichlorophenyl)-ethenyl]-3,4,5,6-tetrahydro-4-hydroxy | cis-6-[2-(2,4-dichlorophenyl)-ethyl]-3,4,5,6-tetrahydro-4-hydroxy-2H-pyran-2-one | oil | C H | 54.00 4.88 | 53.89 4.90 |
| trans-(E)-6-[2-([1,1'-biphenyl]-2-yl)ethenyl]-3,4,5,6-tetrahydro-4-hydroxy | trans-6-[2-([1,1'-biphenyl]-2-yl)-ethyl]-3,4,5,6-tetrahydro-4-hydroxy-2H-pyran-2-one | oil | C H | 77.00 6.80 | 77.17 6.85 |
| cis-(E)-6-[2-(2,4-dichloro-6-phenylmethoxyphenyl)ethenyl]-3,4,5,6-tetrahydro-4-hydroxy | cis-6-[2-(2,4-dichloro-6-phenylmethoxyphenyl)ethyl]-3,4,5,6-tetrahydro-4-hydroxy-2H-pyran-2-one | 96–98 | C H | 60.77 5.10 | 60.73 5.24 |
| trans-(E)-6-[2-(2,4-dichloro-6-cyclohexylmethoxyphenyl)ethenyl]-3,4,5,6-tetrahydro-4-hydroxy | trans-6-[2-(2,4-dichloro-6-cyclohexylmethoxyphenyl)-ethyl]-3,4,5,6-tetrahydro-4-hydroxy-2H-pyran-2-one | 154–155 | C H | 59.85 6.53 | 59.87 6.44 |
| trans-(E)-6-[2-(2,4-dichloro-6-phenoxyphenyl)ethenyl]-3,4,5,6-tetrahydro-4-hydroxy | trans-6-[2-(2,4-dichloro-6-phenoxyphenyl)ethyl]-3,4,5,6-tetrahydro-4-hydroxy-2H-pyran-2-one | oil | C H | 59.85 4.76 | 59.84 5.10 |
| trans-(E)-6-{2-[2,4-dichloro-6-(4-fluorophenylmethoxy)phenyl]ethenyl}-3,4,5,6-tetrahydro-4-hydroxy | trans-6-{2-[2,4-dichloro-6-(4-fluorophenylmethoxy)phenyl]ethyl}-3,4,5,6-tetrahydro-4-hydroxy-2H-pyran-2-one | 151–152 | C H | 58.12 4.63 | 58.13 4.68 |
| trans-(E)-6-{2-[2,4- | trans-b-{2-[2,4-dichloro- | 98– | C | 58.12 | 58.24 |

| 2H-Pyran-2-one | End Product | M.P. °C. | | Calc. | Fd. |
|---|---|---|---|---|---|
| dichloro-6-(2-fluoro-phenylmethoxy)phenyl]-ethenyl}-3,4,5,6-tetra-hydro-4-hydroxy | 6-(2-fluorophenylmethoxy)-phenyl]ethyl}-3,4,5,6-tetra-hydro-4-hydroxy-2H-pyran-2-one | 100 | H | 4.63 | 4.63 |
| trans-(E)-6-{2-[2,4-dichloro-6-(3-fluoro-phenylmethoxy)phenyl]-ethenyl}-3,4,5,6-tetra-hydro-4-hydroxy | trans-6-{2-[2,4-dichloro-6-(3-fluorophenylmethoxy)-phenyl]ethyl}-3,4,5,6-tetra-hydro-4-hydroxy-2H-pyran-2-one | 106–115 | C H | 58.12 4.63 | 58.20 4.72 |

EXAMPLE 10

Preparation of (E)-6-[2-(3,4-Dichlorophenyl)ethenyl]-3,4,5,6-tetrahydro-4-hydroxy-2H-pyran-2-one

Step A. Preparation of (E)-3,4-Dichlorocinnamaldehyde

The reaction mixture containing sodium tetrahydrodiborate (0.76 g, 20 mmole), cadmium chloride.2.5 dimethylformamide (3.7 g, 12.6 mmole) and hexamethylphosphoramide (5 ml) in acetonitrile (100 ml) was stirred magnetically at 0° C. for 5 minutes. A solution of (E)-3-phenyl-2-propenoyl chloride (4.7 g, 20 mmole) in acetonitrile (25 ml) was rapidly added to the stirred reaction mixture and stirring was continued for 5 minutes. The reaction mixture was quenched with 6 N hydrochloric acid and poured into water (500 ml). This aqueous mixture was extracted with ether (3×200 ml). The ether extracts were combined, washed with brine (3×100 ml), dried over magnesium sulfate and filtered. The filtrate was evaporated in vacuo leaving the title compound as a yellow solid. This yellow solid was chromatographed on a silica gel column (200 g). Elution with methylene chloride (500 ml) provided a forerun which was discarded. Continued elution with the same eluant (550 ml) gave the title compound as a light yellow solid (2.2 g, 54%), melting at 92°–94° C.: pmr (CDCl$_3$) δ6.6 (H, dd), 9.72 (H, d).

Step B. Preparation of (E)-6-[2-(3,4-Dichlorophenyl)ethenyl]-3,4,5,6-tetrahydro-4-hydroxy-2H-pyran-2-one By substituting an equimolar amount of (E)-3,4-dichlorocinnamaldehyde for (E)-2,4-dichloro-6-phenylmethoxycinnamaldehyde in Step C of Example 1 and following the procedure for Steps C through F, there was obtained a corresponding amount of the title compound.
trans isomer: mp 116°–118° C.

Analysis Calc. for C$_{13}$H$_{12}$Cl$_2$O$_3$: Calc.: C, 54.37; H, 4.21; Found: C, 54.60; H, 3.96.

EXAMPLE 11

Preparation of Trans-(E)-6-[2-(2,4-dichloro-6-phenoxyphenyl)ethenyl]-3,4,5,6-tetrahydro-4-hydroxy-2H-pyran-2-one

Step A. Preparation of 2,4-Dichloro-6-phenoxybenzaldehyde

Sodium methoxide (0.54 g, 10 mmole) was added to a stirred solution containing 4,6-dichlorosalicylaldehyde (1.9 g, 10 mmole) in methanol (15 ml). After stirring the reaction solution for 15 minutes at 25° C., diphenyliodonium chloride (3.16 g, 10 mmole) was added in one portion. The resulting reaction mixture was refluxed for 30 hours and then concentrated in vacuo. The residue was suspended in water (100 ml) and the mixture was extracted with ether (3×50 ml). The ether extracts were combined, washed with brine (2×50 ml), dried over magnesium sulfate and filtered. The filtrate was evaporated in vacuo leaving the title compound as a brown oil which solidified upon trituration with hexane. This solid was recrystallized from hexane to give pale yellow needles (0.8 g, 30%) which melted at 99°–101° C., pmr (CDCl$_3$) δ6.68 (H, d), 7.28 (6H, m), 10.58 (H, s).

Analysis Calc. for C$_{13}$H$_8$Cl$_2$O$_2$: Calc.: C, 58.45; H, 3.02; Found: C, 58.26; H, 3.01.

Step B. Preparation of Trans-(E)-6-[2-(2,4-dichloro-6-phenoxyphenyl)ethenyl]-3,4,5,6-tetrahydro-4-hydroxy-2H-pyran-2-one By substituting an equimolar amount of 2,4-dichloro-6-phenoxybenzaldehyde in place of 2,4-dichloro-6-phenylmethoxybenzaldehyde in Step B of Example 1 and following the procedure for Steps B through F, there was obtained a corresponding amount of the title compound: trans isomer, mp 124°–126° C.

Analysis Calc. for C$_{19}$H$_{16}$Cl$_2$O$_4$: Calc.: C, 60.17; H, 4.25; Found: C, 60.33; H, 4.30.

EXAMPLE 12

By substituting an equimolar amount of the following substituted diphenyliodonium chlorides for diphenyliodonium chloride in Step A of Example 11 and following essentially the procedure of Steps A and B in Example 11, there was obtained a corresponding amount of the following end product.

| Substituents on Diphenyliodonium chloride | End Product |
|---|---|
| 4,4'-difluoro | trans-(E)-6-{2-[2,4-dichloro-6-(4-fluorophenoxy)phenyl]-ethenyl}-3,4,5,6-tetrahydro-4-hydroxy-2H-pyran-2-one |
| 2,2'-methoxy | trans-(E)-6-{2-[2,4-dichloro-6-(2-methoxyphenoxy)phenyl]-ethenyl}-3,4,5,6-tetrahydro-4-hydroxy-2H-pyran-2-one |
| 4,4'-dimethyl | trans-(E)-6-{2-[2,4-dichloro-6-(4-methylphenoxy)phenyl]-ethenyl}-3,4,5,6-tetrahydro-4-hydroxy-2H-pyran-2-one |

EXAMPLE 13

Resolution of the Optical Isomers of (±)Trans-(E)-6-[2-(2,4-dichlorophenyl)ethenyl]-3,4,5,6-tetrahydro-4-hydroxy-2H-pyran-2-one

Step A. Preparation and Separation of Diastereomeric Amides (Diastereomers A and B)

A solution of (±)-trans-(E)-6-[2-(2,4-dichlorophenyl)ethenyl]-3,4,5,6-tetrahydro-4-hydroxy-2H-pyran-2-one (2.87 g, 10 mmole) in d-(+)-α-methylbenzylamine (15 ml) was stirred for 18 hours at 25° C. and then poured into water (100 ml). This aqueous mixture was acidified with 6 N hydrochloric acid and then extracted with ether (3×100 ml). The ether extracts were combined, washed with brine (4×75 ml), dried over magnesium sulfate and filtered. Evaporation of the filtrate in vacuo gave the intermediate diastereomeric amides as a tan viscous oil (4.1 g).

The tan viscous oil (3.1 g, 7.6 mmole) was chromatographed on a silica gel column (200 g). Elution with acetone-methylene chloride (1:4, v:v; 1200 ml) gave a forerun which was discarded. Continued elution with the same eluant (1000 ml) gave the diastereomeric amides as a viscous oil (3.0 g).

The diastereomeric amides were separated by chromatography on a Waters Prep LC500. The separation was accomplished by using two prep PAK-500 silica cartridges in series and eluting with acetone-methylene chloride (1:4, v:v). Using the shave-recycle technique, diastereomer A (1.36 g) and diastereomer B (1.20 g) were obtained.

Recrystallization of diastereomer A from n-butyl chloride gave colorless clusters (1.0 g) which melted at 106°–108° C.: pmr (CDCl$_3$) δ1.47 (3H, d), 2.33 (2H, d), 4.30 (H, m), 5.17 (H, q), 7.33 (8H, m).

Analysis Calc. for C$_{21}$H$_{23}$Cl$_2$NO$_3$: Calc.: C, 61.77; H, 5.68; N, 3.43; Found: C, 61.78; H, 5.78; N, 3.50.

Recrystallization of diastereomer B from n-butyl chloride-petroleum ether gave a pale yellow solid which melted at 55°–60° C.: pmr (CDCl$_3$) δ1.47 (3H, d), 2.33 (2H, d), 4.30 (H, m), 5.17 (H, q), 7.33 (8H, m).

Analysis Calc. for C$_{21}$H$_{23}$Cl$_2$NO$_3$: Calc.: C, 61.77; H, 5.68; N, 3.43; Found: C, 61.41; H, 5.87; N, 3.30.

Step B. Preparation of (+)-Trans-(E)-6-[2-(2,4-dichlorophenyl)ethenyl]-3,4,5,6-tetrahydro-4-hydroxy-2H-pyran-2-one Diastereomer A (0.74 g, 1.8 mmole) of Step A was dissolved in 95% ethanol (25 ml) containing 1 N sodium hydroxide (3.6 ml, 3.6 mmole) and the solution was refluxed for 54 hours. The solvent was removed in vacuo and the residue was suspended in water (100 ml) and acidified with 6 N hydrochloric acid. This aqueous mixture was extracted with ether (3×75 ml). The ether extracts were combined, washed with brine (2×50 ml), dried over magnesium sulfate and filtered. The filtrate was evaporated in vacuo leaving the intermediate acid as a yellow oil (0.54 g).

A solution of the yellow oil in toluene (150 ml) was refluxed through a soxhlet containing molecular sieves (3 Å) for 5 hours. The solution was evaporated in vacuo leaving the title compound as a yellow solid. The title compound was purified by recrystallization from ether and then n-butyl chloride to give white needles (0.11 g, 20%) melting at 114°–115° C., pmr (CDCl$_3$) δ2.03 (2H, m), 2.73 (2H, m), 4.46 (H, m), 5.41 (H, m), 6.19 (H, dd), 7.01 (H, d), 7.14–7.50 (3H, m).

Analysis Calc. for C$_{13}$H$_{12}$Cl$_2$O$_3$: Calc.: C, 54.37; H, 4.21; Found: C, 54.51; H, 4.32.

[α]$_D^{25}$ = +5.9° (c 0.425; chloroform)

Step C. Preparation of (−)-Trans-(E)-6-[2-(2,4-Dichlorophenyl)ethenyl]-3,4,5,6-tetrahydro-4-hydroxy-2H-pyran-2-one Diastereomer B (1.1 g, 2.7 mmole) of Step A was dissolved in 95% ethanol (25 ml) containing 1 N sodium hydroxide (5.4 ml, 5.4 mmole) and the solution was refluxed for 18 hours. The ethanol was removed in vacuo and the residue was suspended in water (100 ml) and acidified with 6 N hydrochloric acid. This aqueous mixture was extracted with ether (2×100 ml). The ether extracts were combined, washed with brine (3×50 ml), dried over magnesium sulfate and filtered. The filtrate was evaporated in vacuo leaving the intermediate acid as a yellow oil (0.85 g).

A solution of the yellow oil in toluene (150 ml) was refluxed through a soxhlet containing molecular sieves (3 Å) for 5 hours. The solution was evaporated in vacuo leaving the title compound as a yellow solid. The title compound was recrystallized twice from n-butyl chloride to give white needles (0.34 g, 44%) melting at 114°–115° C.: pmr (CDCl$_3$) δ2.03 (2H, m), 2.73 (2H, m), 4.46 (H, m), 5.41 (H, m), 6.19 (H, dd), 7.01 (H, d), 7.14–7.50 (3H, m).

Analysis Calc. for C$_{13}$H$_{12}$Cl$_2$O$_3$: Calc.: C, 54.37; H, 4.21; Found: C, 54.31; H, 4.26.

[α]$_D^{25}$ = −6.6° (c 0.555; chloroform)

EXAMPLE 14

Resolution of the Optical Isomers of (±) Trans-6-[2-2,4-dichloro-6-phenylmethoxyphenyl)ethyl]-3,4,5,6-tetrahydro-4-hydroxy-2H-pyran-2-one

Step A. Preparation and Separation of Diastereomeric Amides (Diastereomers A and B)

By substituting an equimolar amount of (±) trans-6-[2-(2,4-dichloro-6-phenylmethoxyphenyl)ethyl]-3,4,5,6-tetrahydro-4-hydroxy-2H-pyran-2-one for (±) trans-(E)-6-[2-(2,4-dichlorophenyl)ethenyl]-3,4,5,6-tetrahydro-4-hydroxy-2H-pyran-2-one and replacing d-(+)-α-methylbenzylamine with the 1-(−)-isomer in Step A of Example 13 and following the procedure described in Step A of Example 13, there was obtained a corresponding amount of the diastereomeric amides:

Diastereomer A: mp 177°–179° C.; pmr (CDCl$_3$) δ1.45 (3H, d), 2.22 (2H, d), 2.83 (2H, m), 3.74 (H, m), 4.13 (H, m), 5.04 (2H, s), 6.86 (H, d), 7.05 (H,d), 7.33 (5H, s), 7.82 (5H,s)

Analysis Calc. for C$_{28}$H$_{31}$Cl$_2$NO$_4$: Calc.: C, 65.11; H, 6.05; N, 2.71; Found: C, 65.28; H, 6.34; N, 2.95

Diastereomer B: mp 130°–132° C.; pmr (CDCl$_3$) δ1.45 (3H,d), 2.22 (2H,d), 2.83 (2H, m), 3.74 (H, m), 4.13 (H, m), 5.04 (2H, s), 6.86 (H,d), 7.05 (H, d), 7.33 (5H, s), 7.82 (5H, s).

Analysis Calc. for C$_{28}$H$_{31}$Cl$_2$NO$_4$: Calc.: C, 65.11; H, 6.05; N, 2.71; Found: C, 65.24; H, 6.27; N, 2.88

Step B. Preparation of (+)-Trans-6-[2-(2,4-dichloro-6-phenylmethoxyphenyl)ethyl]-3,4,5,6-tetrahydro-4-hydroxy-2H-pyran-2-one. 0.1 n-Butyl Chloride Solvate By substituting an equimolar amount of diastereomer A from the preceeding step for diastereomer A in Step B of Example 13 and following the procedure described therein, there was obtained a corresponding amount of the title compound, mp 108°–112° C.; pmr (CDCl$_3$) δ1.91 (4H, m), 2.61 (2H, m), 2.93 (2H, m), 4.30 (H, m), 4.70 (H, m), 5.06 (2H, s), 6.33 (H, d), 7.02 (H, d), 7.43 (5H, s).

Analysis Calc. for C$_{20}$H$_{20}$Cl$_2$O$_4$.0.1C$_4$H$_9$Cl; Calc.: C, 60.56; H, 5.21; Found: C, 60.93; H, 5.73

$[\alpha]_D^{25} = +16.6°$ (c, 0.1; chloroform)

Step C. Preparation of (−)-Trans-6-[2-(2,4-dichloro-6-phenylmethoxyphenyl)ethyl]-3,4,5,6-tetrahydro-4-hydroxy-2H-pyran-2-one.0.1 n-Butyl Chloride Solvate By substituting an equimolar amount of diastereomer B from Step A above for diastereomer B in Step C of Example 13 and following the procedure described therein, there was obtained a corresponding amount of the title compound, mp 104°–111° C.; pmr (CDCl$_3$) δ1.91 (4H, m), 2.61 (2H, m), 2.93 (2H,m), 4.30 (H, m), 4.70 (H, m), 5.06 (2H, s), 6.33 (H, d) 7.02 (H, d), 7.43 (5H, s).

Analysis Calc. for C$_{20}$H$_{20}$Cl$_2$O$_4$.0.1 C$_4$H$_9$Cl; Calc.: C, 60.56; H, 5.21; Found: C, 60.62; H, 5.46

$[\alpha]_D^{25} = -17.7°$ (c, 0.1; chloroform)

EXAMPLE 15

Preparation of (E)-6-[2-(2,6-Dichlorophenyl)ethenyl]-3,4,5,6-tetrahydro-4-hydroxy-4-methyl-2H-pyran-2-one

Step A. Preparation of 6-(2,4-Dichlorophenyl)-4-hydroxy-5-hexene-2-one

2-Acetoxypropene (3.3 ml, 30 mmole) and tri-n-butyltin methoxide (5.7 g, 24 mmole) were combined and stirred at 60°–70° C. under N$_2$ for 1 hour then placed under vacuum for an additional 30 minutes. 3-(2,4-Dichlorophenyl)propenal (4 g, 20 mmole) was added and the reaction mixture was stirred at 70° C. under N$_2$ for 4 hours. The clear reaction mixture was then cooled, treated with malonic acid (1 g, 10 mmole) in ether (20 ml) and refluxed for 30 minutes. After cooling to −20° C., the reaction mixture was filtered and the precipitate was washed with ether (4×10 ml). The ethereal solutions were combined, evaporated and the residual oil was chromatographed on a 60 mm column with 15 cm of silica gel (230–400 mesh). Elution with chloroform-methanol (99:1, v:v; 2.0 L) provided the title compound as a thick yellow oil (4.2 g, 81%); pmr CDCl$_3$) 2.2 (3H, s), 2.73 (2H, d), 4.73 (H, m), 6.10 (H, dd).

Analysis Calc. for C$_{12}$H$_{12}$Cl$_2$O$_2$: Calc.: C, 55.62; H, 4.67; Found: C, 55.55; H, 4.72

Step B. Preparation of 6-(2,4-Dichlorophenyl)-2-oxo-5-hexene-4-yl 2-Bromoacetate 2-Bromoacetyl bromide (1.1 ml, 13.2 mmole) was added dropwise to a stirred solution of 6-(2,4-dichlorophenyl)-4-hydroxy-5-hexene-2-one (3.4 g, 13.1 mmole) and pyridine (1.07 ml, 13.2 mmole) in ether (100 ml) at 0° C. The ice bath was removed and the reaction mixture was stirred at 20° C. for 2 hours and then diluted with H$_2$O (100 ml). The organic layer was separated and washed with 1 N HCl (100 ml), H$_2$O (2×100 ml) and brine, dried over MgSO$_4$, filtered and evaporated. The residual oil was chromatographed on a 60 mm column with 15 cm of silica gel (230–400 mesh) Elution with methylene chloride-acetone (99:1; v:v; 1.9 L) provided the title compound (2.8 g, 56%); pmr (CDCl$_3$) δ2.2 (3H, s), 2.92 (2H, t), 3.85 (2H, s), 5.9 (H, m), 6.15 (H, m) 6.95–7.5 (4H, m).

Step C. Preparation of (E)-6-[2-(2,5-Dichlorophenyl)ethenyl]-3,4,5,6-tetrahydro-4-hydroxy-4-methyl-2H-pyran-2-one A solution of 6-(2,4-dichlorophenyl)-2-oxo-5-hexene-4-yl 2-bromoacetate (2.8 g, 7.4 mmole) in dry THF (50 ml) was added dropwise to a vigorously stirred slurry of activated zinc dust (720 mg, 11.1 mmole), cuprous bromide (60 mg, 0.4 mmole), diethylaluminum chloride (25% solution in toluene; 3.2 ml, 8 mmole) and dry THF (50 ml) under N$_2$ at 20° C. Stirring was continued for 5 hours before quenching with pyridine (8 ml) followed by addition of H$_2$O (500 ml) and ether extraction (3×150 ml). The combined ether extracts were washed with 1 N HCL (2×50 ml), H$_2$O (2×250 ml) and brine, then dried (MgSO$_4$), filtered and evaporated in vacuo leaving a sticky, pale yellow solid (1.8 g) which is a mixture of cis and trans isomers of the title compound. This crude product was digested once with ether (40 ml) and then crystallized from n-butyl chloride (25 ml) to provide the trans isomer of the title compound as tiny, colorless crystals (550 mg), mp 136°–138° C.

Analysis Calc. for C$_{14}$H$_{14}$Cl$_2$O$_3$: Calc.: C, 55.83; H, 4.69; Found: C, 56.07; H, 4.66

The filtrates from digestion and crystallization vida supra were combined, evaporated and chromatographed using a Waters Prep LC500. The separation was accomplished by using two prep PAK 500/silica cartridges in series and eluting with methylene chloride-acetone (15:1, v:v). By using the shave-recycle technique, the cis (220 mg) and the trans (230 mg) isomers of the title compound were separated. The cis isomer of the title compound was crystallized from n-butyl chloride-hexane (2:1, v:v) to give 120 mg of solid, mp 135°–137° C.

Analysis Calc. for C$_{14}$H$_{14}$Cl$_2$O$_3$: Calc.: C, 55.83; H, 4.69; Found: C, 55.46; H, 4.71.

The epimeric alcohols are readily distinguished by analytical TLC (fluorescent silica gel (40 Å), 1×3 in, MK6F, Whatman) and elution with methylene chloride-acetone (9:1; v:v: cis alcohol, R$_f$0.25; trans alcohol, R$_f$0.30.

EXAMPLE 16

Alternate Route to (E)-6-[2-(2,6-Dichlorophenyl)ethenyl]-3,4,5,6-tetrahydro-4-hydroxy-4-methyl-2H-pyran-2-one

Step A. Preparation of 6-(2,4-Dichlorophenyl)-2-oxo-5-hexene-4-yl Acetate

Acetyl chloride (1.2 ml, 16.5 mmole) was added dropwise to a stirred solution of 6-(2,4-dichlorophenyl)-4-hydroxy-5-hexene-2-one (3.9 g, 15 mmole) in pyridine (60 ml) at 0° C. The ice bath was removed, and the reaction mixture was stirred at 20° C. for 2 hours and then diluted with ether (300 ml). The ether solution was washed with 1 N HCl (3×300 ml) and saturated NaHCO$_3$, dried over MgSO$_4$, filtered and evaporated. The residual pale amber oil (4.1 g) was chromatographed on a 50 mm column with 15 cm of silica gel (230–400 mesh). Elution with methylene chloride (2 L) provided the title compound as a pale yellow oil (3.95 g, 87%): pmr (CDCl$_3$) δ2.03 (3H, s), 2.17 (3H, s), 2.83 (2H, dd).

Analysis Calc. for C$_{14}$H$_{14}$Cl$_2$O$_3$: Calc.: C, 55.83; H, 4.69; Found: C, 55.82; H, 4.76

Step B. Preparation of Ethyl 5-Acetoxy-7-(2,4-dichlorophenyl)-3-hydroxy-3-methyl-6-heptenoate A solution of 6-(2,4-dichlorophenyl)-2-oxo-5-hexene-4-yl acetate (1.3 g, 4.3 mmole) and ethyl bromoacetate (0.47 ml, 4.2 mmole) in dry THF (10 ml) was added dropwise to a vigorously stirred slurry of activated zinc dust (490 mg, 7.5 mmoles), cuprous bromide (29 mg, 0.2 mmole), diethylaluminum chloride (25% solution in toluene; 1.72 ml, 4.3 mmole) and dry THF (5 ml) under $N_2$ at 20° C. Stirring was continued for 5 hours before quenching with pyridine (3.5 ml). After the addition of water (50 ml) the mixture was extracted with ether (3×80 ml). The combined ether extracts were washed with 1 N HCl (2×25 ml), $H_2O$ (2×50 ml) and brine, then dried ($MgSO_4$), filtered and evaporated leaving the crude title compound as a pale yellow oil (1.2 g); pmr ($CDCl_3$) $\delta 1.28$ (3H, t), 1.33 (3H, t), 2.10 (3H, s).

Step C. Preparation of (E)-6-[2-(2,6-Dichlorophenyl)ethenyl]-3,4,5,6-tetrahydro-4-hydroxy-4-methyl-2H-pyran-2-one Ethyl 5-acetoxy-7-(2,4-dichlorophenyl)-3-hydroxy-3-methyl-6-heptenoate (1.2 g, 3.2 mmole) was stirred with 1 N NaOH (6.4 ml, 6.4 mmole) at 50° C. for 1 hour. The aqueous solution was diluted with $H_2O$ (50 ml) and washed with ether (2×50 ml). The aqueous layer was acidified with 12 N HCl and extracted with ether (2×50 ml). The combined organic extracts were washed with brine, dried over $MgSO_4$, filtered and evaporated leaving the crude diol acid which was lactonized by refluxing in toluene (75 ml) under a Soxhlet extractor filled with 3 Å sieves for 3 hours. The toluene was evaporated and the residue was chromatographed on a 50 mm column with 15 cm of silica gel (230–400 mesh). Elution with chloroform-methanol (19:1; v:v; 400 ml) provided (120 mg, 12%) of the title compound as a mixture of cis (46%) and trans (54%) isomers as determined by HPLC.

EXAMPLE 17

Preparation of (E)-6-[2-(2'-methoxy-[1,1'-biphenyl]-2-yl)ethenyl]-3,4,5,6-tetrahydro-4-hydroxy-2H-pyran-2-one.

Step A. Preparation of 2-(2'-Methoxy-[1,1'-biphenyl]-2-yl)-4,4-dimethyl-2-oxazoline.

2-Methoxyphenylmagnesium bromide, prepared from 2-bromoanisole (22.4 g, 120 mmol) and magnesium (2.9 g, 120 mmol), in dry THF (75 ml) was added dropwise to a stirred solution of 2-(2-methoxyphenyl)-4,4-dimethyl-2-oxazoline (20.4 g, 100 mmol) in dry THF (150 ml) under $N_2$ at 20° C. Stirring of the solution was continued for 20 hours and then the reaction mixture was quenched by the addition of saturated ammonium chloride solution. The resulting mixture was extracted with ether (2×500 ml), dried over $MgSO_4$, filtered and evaporated. The residue was chromatographed on silica gel (ethyl acetate-hexane) to provide title compound as colorless crystals (25.3 g, 90%), mp 129°–131° C.

Step B. Preparation of 2'-Methoxy-[1,1'-biphenyl]-2-carboxylic acid.

2-(2'-Methoxy-[1,1'-biphenyl]-2-yl)-4,4-dimethyl-2-oxazoline (25 g, 90 mmol) was dissolved in 4.5 N HCl (1.5 L) and heated at reflux for 20 hours. After cooling, the heterogeneous mixture was extracted with ether (3×200 ml). The etheral extracts were combined and washed with $H_2O$ and brine, dried over $MgSO_4$, filtered and then evaporated to provide the title compound (15.4 g, 75%), mp 196°–197° C., as a colorless solid.

Step C. Preparation of 2'-Methoxy-[1,1'-biphenyl]-2-carbonyl Chloride.

2'-Methoxy-[1,1'-biphenyl]-2-carboxylic acid (32 g., 100 mmole) was dissolved in thionyl chloride (40 ml) and the solution was refluxed for 3 hours. The solution was evaporated to provide the title compound.

Step D. Preparation of (E)-6-[2-(2'-Methoxy-[1,1'-biphenyl]-2-yl)ethenyl]-3,4,5,6-tetrahydro-4-hydroxy-2H-pyran-2-one.

Starting with 2'-methoxy-[1,1'-biphenyl]-2-carbonyl chloride in place of 2,3-dichlorobenzoyl chloride, the title compound was prepared following the procedures of Examples 6, Step A, and then Example 1, Steps C through F.

EXAMPLE 18

Preparation of (E)-6-[2-(4'-chloro-[1,1'-biphenyl]-2-yl)ethenyl]-3,4,5,6-tetrahydro-4-hydroxy-2H-pyran-2-one Starting with 4-chlorophenylmagnesium bromide, in place of the 2-methoxyphenylmagnesium bromide, the title compound was prepared following the procedure of Example 17, Steps A through D.

EXAMPLE 19

Preparation of (E)-6-[2-(4'-Fluoro-[1,1'-biphenyl]-2-yl)ethenyl]-3,4,5,6-tetrahydro-4-hydroxy-2H-pyran-2-one Starting with 4-fluorophenylmagnesium bromide, in place of the 2-methoxyphenylmagnesium bromide, the title compound was prepared following the procedure of Example 17, Steps A through D.

EXAMPLE 20

Preparation of (E)-6-[2-(4'-methyl-[1,1'-biphenyl]-2-yl)ethenyl]-3,4,5,6-tetrahydro-4-hydroxy-2H-pyran-2-one.

Starting with 4-methylphenylmagnesium bromide, in place of the 2-methoxyphenylmagnesium bromide, the title compound was prepared following the procedure of Example 17, Steps A through D.

EXAMPLE 21

Preparation of 6-[2-(2,4-Dichloro-6-hydroxyphenyl)ethyl]-3,4,5,6-tetrahydro-4-hydroxy-2H-pyran-2-one

Step A. Preparation of 6-{2-[2,4-Dichloro-6-(2-methoxyethoxymethoxy)-phenyl]ethyl}-3,4,5,6-tetrahydro-4-hydroxy-2H-pyran-2-one.

Starting with (E)-6-{2-[2,4-Dichloro-6-(2-methoxyethoxymethoxy)phenyl]ethenyl}-3,4,5,6-tetrahydro-4-hydroxy-2H-pyran-2-one and following the procedure of Example 8, the title compound was obtained as a viscous golden oil: pmr ($CDCl_3$) $\delta 2.63$ (2H, d), 3.36 (3H, s), 3.55 (2H, m), 3.8 (2H m), 4.35 (H, m), 4.73 (H, m), 5.27 (2H, s), 7.6 (2H, dd).

Step B. Preparation of 6-{2-(2,4-Dichloro-6-hydroxyphenyl)ethyl}-3,4,5,6-tetrahydro-4-hydroxy-2H-pyran-2-one Zinc bromide (2.4 g, 10 mmole) was added to a solution of 6-{2-[2,4-dichloro-6-(2-methoxyethoxymethoxy)phenyl]ethyl}-3,4,5,6-tetrahydro-4-hydroxy-2H-pyran-2-one (780 mg, 2 mmole) in methylene chloride (12 ml). The resulting mixture was stirred at 20° C. for 2 hours, then quenched with saturated sodium bicarbonate solution (50 ml) and diluted with ether (200 ml). The ethereal layer was washed with brine, dried over $MgSO_4$, filtered and evaporated. The residue was chromatographed on a 50 mm low-pressure column with 6 inches of silica gel (230–400 mesh). The column was eluted with 470 ml of methylene chloride-acetone (4:1, v:v). The next 330 ml provided the title compound as a golden glass (100 mg., 16%): pmr ($CDCl_3$) δ2.62 (2H, d), 4.29 (H, m), 4.78 (H, m), 6.87 (2H, s).

EXAMPLE 22

Preparation of 6-{2-[2,4-Dichloro-6-(4-trifluoromethylphenylmethoxy)phenyl]ethyl}-3,4,5,6-tetrahydro-4-hydroxy-2H-pyran-2-one.

By following the procedure of Example 1, step A, but substituting equimolar amounts of 6-{2-(2,4-dichloro-6-hydroxyphenyl)ethyl}-3,4,5,6-tetrahydro-4-hydroxy-2H-pyran-2-one and 4-trifluoromethylbenzyl bromide for the 4,6-dichlorosalicylaldehyde and benzyl bromide used therein, the title compound is obtained, m.p. 104°–105° C.

EXAMPLE 23

Preparation of 6-[2-(2-acetoxy-4,6-dichlorophenyl)ethyl]-3,4,5,6-tetrahydro-4-hydroxy-2H-pyran-2-one.

Acetyl chloride (0.08 ml, 1.05 mmole) was added dropwise to a stirred solution of 6-[2-(2,4-dichloro-6-hydroxyphenyl)ethyl]-3,4,5,6-tetrahydro-4-hydroxy-2H-pyran-2-one (300 mg, 1 mmole) and pyridine (0.09 ml, 1.05 mmole) in ether (10 ml) at 0° C. The ice bath was removed and the reaction mixture was stirred at 20° C. for 1 hour and then diluted with $H_2O$ (10 ml). The organic layer was separated and washed with 1 N HCl (10 ml), $H_2O$ (2×10 ml) and brine, dried over $MgSO_4$, filtered and evaporated to provide the title compound.

EXAMPLE 24

Preparation of 6-[2-(2-Benzoyloxy-4,6-dichlorophenyl)ethyl]-3,4,5,6-tetrahydro-4-hydroxy-2H-pyran-2-one.

By following the procedure of Example 23, but substituting an equivalent amount of benzoyl chloride for the acetyl chloride used therein, the title compound is obtained.

EXAMPLE 25

Preparation of (E)-Trans-6-[2-(3-trifluoromethylphenyl)ethenyl]-3,4,5,6-tetrahydro-4-hydroxy-2H-pyran-2-one.

By substituting an equimolar amount of 3-trifluoromethylbenzaldehyde for 2,4-dichloro-6-phenylmethoxybenzaldehyde in step B of Example 1 and following Steps B through F, there is obtained a corresponding amount of the title compound.

EXAMPLE 26

Preparation of Trans-6-(2-chlorophenylmethyl)-3,4,5,6-tetrahydro-4-hydroxy-2H-pyran-2-one.

By substituting an equimolar amount of o-chlorophenylacetaldehyde for 2,4-dichloro-6-phenylmethoxybenzaldehyde in step C of Example 1 and following Steps C through F there is obtained a corresponding amount of the title compound.

EXAMPLE 27

Preparation of (E)-6-[2-(2,4-dichloro-6-methoxyphenylethenyl]-3,4,5,6-tetrahydro-4-hydroxy-2H-pyran-2-one.

The procedure of Example 1 is followed using an equivalent amount of methyl iodide in place of benzyl bromide in Step A. The compound named above is obtained.

EXAMPLE 28

Preparation of (E)-6-[2-(2,4-dichloro-6-cyclopropylmethoxyphenyl)ethenyl]-3,4,5,6-tetrahydro-4-hydroxy-2H-pyran-2-one.

The procedure of Example 1 is followed using an equivalent amount of cyclopropylmethyl iodide in place of benzyl bromide in Step A. The above named compound is obtained.

EXAMPLE 29

Trans-6-(3-phenylpropyl)-3,4,5,6-tetrahydro-4-hydroxy-2H-pyran-2-one.

Step A. Preparation of 4-Phenylbutyronitrile

A mixture of 1-bromo-4-phenylbutane (58.8 g, 0.24 mole) and sodium cyanide (25 g, 0.5 mole) in ethanol (300 ml)-water (100 ml) is heated at reflux with stirring for 5 hours. The resulting reaction mixture is concentrated in vacuo and extracted with ether. The ethereal extract is filtered and evaporated at reduced pressure to afford the title compound which is purified by distillation.

Step B. Preparation of 4-Phenyl-1-butanal

To a stirred suspension of 4-phenylbutyronitrile (21.7 g, 0.12 mole) in ether (400 ml) at 78° C. is added 85 ml. of 25.3% diisobutylaluminum hydride in toluene over a period of 1 hour. After an additional 1 hour, the dry ice-acetone bath is removed and the reaction mixture is stirred at ambient temperature for 3 hours. The reaction mixture is added slowly to 5% aqueous sulfuric acid and then is extracted with several portions of ether. The ether extracts are combined, washed with water and saturated aqueous sodium chloride solution and dried over magnesium sulfate. After removal of the ether, the residual yellow oil is distilled in vacuo to give an oil.

Step C. Trans-6-(3-phenylpropyl)-3,4,5,6-tetrahydro-4-hydroxy-2H-pyran-2-one.

This product is prepared from 4-phenyl-1-butanal in a manner similar to Steps C, D and E in Example 1. The product is purified by column chromatography and high pressure liquid chromatography to give the title compound.

EXAMPLE 30

Preparation of
6-{2-[6-[(4-acetoxyphenyl)methoxy]-2,4-dichlorophenyl]ethyl}-3,4,5,6-tetrahydro-4-hydroxy-2H-pyran-2-one.

By following the procedure of Example 1, Step A, but substituting equimolar amounts of 6-[2-(2,4-dichloro-6-hydroxyphenyl)ethyl]-3,4,5,6-tetrahydro-4-hydroxy-2H-pyran-2-one and 4-(bromomethyl)phenol acetate for the 4,6-dichlorosalicylaldehyde and benzyl bromide used therein, the title compound is obtained.

EXAMPLE 31

Preparation of
6-{2-[2,4-Dichloro-6-(4-hydroxyphenylmethoxyphenyl]ethyl}-3,4,5,6-tetrahydro-4-hydroxy-2H-pyran-2-one.

By following the procedure of Example 16, Step C, but substituting an equimolar amount of 6-{2-[6-(4-acetoxyphenylmethoxy)-2,4-dichlorophenyl]ethyl}-3,4,5,6-tetrahydro-4-hydroxy-2H-pyran-2-one for the ethyl 5-acetoxy-7-(2,4-dichlorophenyl)-3-hydroxy-3-methyl-6-heptenoate used therein, the title compound is obtained.

EXAMPLE 32

Preparation of
(E)-trans-6-{2-[3,5-Dichloro-4'-fluoro-2-(1,1'-biphenyl)yl]ethenyl}-3,4,5,6-tetrahydro-4-hydroxy-2H-pyran-2-one.

Step A. Preparation of 2,4-Dichloro-6-methoxybenzaldehyde

By substituting an equimolar amount of methyl iodide for benzyl bromide in Step A of Example 1 there was obtained a corresponding amount of the title compound as a white powder, mp 110°–111° C.

Step B. Preparation of N-(2-Hydroxy-1,1-dimethylethyl)-2,4-dichloro-6-methoxybenzamide A suspension of 2,4-dichloro-6-methoxybenzaldehyde (3 g, 15 mmol) and N-bromosuccinimide (3.6 g, 20 mmol) in carbon tetrachloride (30 ml) was illuminated with a 150 W flood lamp under nitrogen with vigorous stirring on a steam bath for seven minutes. The cloudy mixture was cooled to 0° C., diluted with methylene chloride (30 ml) and treated dropwise with a solution of 2-amino-2-methylpropanol (3 ml, 30 mmol) in methylene chloride (30 ml). The ice bath was removed and the mixture was stirred at 20° C. for twenty hours.

The reaction mixture was filtered and the collected solids were washed with additional methylene chloride (50 ml). The clear filtrates were combined and washed with H$_2$O (100 ml), 5% HCl (100 ml), 5% NaOH (100 ml), H$_2$O (100 ml) and brine, then dried (MgSO$_4$), filtered and evaporated in vacuo to provide the title compound as a white powder (3.6 g, 82%), mp 130°–132° C. Crystallization from hexane-toluene (10:8, v:v) provided an analytical sample of title compound, mp 131°–132° C.

Analysis Calc. for C$_{12}$H$_{15}$Cl$_2$NO$_3$: Calc: C, 49.33 H, 5.18 N, 4.79; Found: C, 49.51 H, 5.27 N, 4.62

Step C. Preparation of 2-(2,4-Dichloro-6-methoxyphenyl)-4,4-dimethyl-2-oxazoline N-(2-Hydroxy-1,1-dimethylethyl)-2,4-dichloro-6-methoxybenzamide (5.5 g, 18.8 mmol) was treated dropwise with thionyl chloride (5.5 ml) and stirred magnetically at 20° C. for 30 min. Dry ether (100 ml) was added, the mixture was stirred for an additional one hour and the oxazoline hydrochloride precipitate was collected by filtration. The salt was neutralized with 20% sodium hydroxide to afford an alkaline mixture which was extracted with ether. The ethereal extract was dried (MgSO$_4$) and concentrated to give an oil (3.6 g, 70%), which crystallized on standing, mp 47°–50° C.

Analysis for C$_{12}$H$_{13}$Cl$_2$NO$_2$: Calc: C, 52.57 H, 4.78 N, 5.11; Found: C, 52.60 H, 4.98 N, 4.99

Step D. Preparation of 2-(3,5-Dichloro-4'-fluoro-2-[1,1'-biphenyl]yl)-4,4-dimethyl-2-oxazoline By substituting equimolar amounts of 2-(2,4-dichloro-6-methoxyphenyl)-4,4-dimethyl-2-oxazoline and 4-fluorophenylmagnesium bromide for 2-(2-methoxyphenyl)-4,4-dimethyl-2-oxazoline and 2-methoxyphenylmagnesium bromide, the title compound was prepared following the procedure of Example 17, Step A, (85%), mp 93°–95° C.

Analysis for C$_{17}$H$_{14}$Cl$_2$FNO: Calc: C, 60.37 H, 4.17 N, 4.14; Found: C, 60.72 H, 4.17 N, 3.89

Step E. Preparation of 2-(3,5-Dichloro-4'-fluoro-2-[1,1'-biphenyl]yl)-3,4,4-trimethyl-2-oxazolium iodide A solution of 2-(3,5-dichloro-4'-fluoro-2-[1,1'-biphenyl]yl)-4,4-dimethyl-2-oxazoline (4.6 g, 13.6 mmol) and methyl iodide (7 ml) in nitromethane (30 ml) was stirred on a steam bath for sixteen hours. The cooled reaction mixture was diluted with dry ether (200 ml) and, after cooling in an ice-bath, the crystalline product was collected to give 6 g (92%) of the title compound, mp 214°–216° C. dec. Crystallization from acetonitrile-ether (1:3, v:v) provided an analytical sample of the title compound, mp 218°–219.5° C. dec.

Analysis for C$_{18}$H$_{17}$Cl$_2$FINO: Calc: C, 45.03 H, 3.57 N, 2.92; Found: C, 44.94 H, 3.47 N, 2.83

Step F. Preparation of 3,5-Dichloro-4'-fluoro-[1,1'-biphenyl]-2-carboxaldehyde A vigorously stirred suspension of 2-(3,5-dichloro-4'-fluoro-2-[1,1'-biphenyl]yl)-3,4,4-trimethyl-2-oxazolium iodide (5.9 g, 12.3 mmol) in ethanol (50 ml) was treated portionwise with sodium borohydride (550 mg, 18 mmol). After stirring for two hours at ambient temperature the clear solution was diluted with 3 N hydrochloric acid (100 ml) and stirred on a steam bath for two hours. The reaction mixture was then cooled, diluted with H$_2$O (200 ml) and extracted with ether (300 ml). The ether extract was washed with H$_2$O (2×200 ml) and brine, then dried (MgSO$_4$), filtered and evaporated in vacuo to provide 2.72 g (82%) of the title compound, mp 66°–68° C. Crystallization from petroleum ether provided an analytical sample of the title compound, mp 73°–74° C.

Analysis for C$_{13}$H$_7$Cl$_2$FO: Calc: C, 58.02 H, 2.62; Found: C, 58.15 H, 2.52

Step G. Preparation of (E)-trans-6-[2-(3,5-dichloro-4'-fluoro-[1,1'-biphenyl]-2-yl)ethenyl]-3,4,5,6-tetrahydro-4-hydroxy-2H-pyran-2-one By substituting an equimolar amount of 3,5-dichloro-4'-fluoro-[1,1'-biphenyl]-2-carboxaldehyde in place of 2,4-dichloro-6-phenylmethoxybenzaldehyde in the alternate to alternate Step B, of Example 1 and then following the procedures of Step B through F, there was obtained a corresponding amount of the title compound, mp 121°–122° C.

Analysis for $C_{19}H_{15}Cl_2FO_3$: Calc: C, 59.86 H, 3.97; Found: C, 59.70 H, 3.97

The cis isomer of the title compound was obtained in comparable yield after crystallization from n-butyl chloride, mp 107°–108° C.

EXAMPLE 33

Starting with 2-(2,4-Dichloro-6-methoxyphenyl)-4,4-dimethyl-2-oxazoline but substituting equimolar amounts of the following Grignard reagents in place of 4-fluorophenylmagnesium bromide in Step D of Example 32 and following the procedures of Steps D through G there was obtained a corresponding amount of the appropriate end product listed below.

pound, mp 203°–205° C: pmr $(CDCl_3)\delta$ 1.73 (3H,S), 6.50 (H, d, J=1.5 Hz) 6.97 (2H, m), 7.12 (H,d, J=1.5 Hz) 7.33 (3H, m), 8.03 (H, S).

Analysis Calc. for $C_{30}H_{22}Cl_2N_4O_4Pd_2$: Calc: C, 43.42 H, 2.67 N, 3.38; Found: C, 43.54 H, 2.59 N, 3.13

Step B. Preparation of 3,5-Dichloro-4'-fluoro-[1,1'-biphenyl]-2-carboxyldehyde A solution of bis-[μ-(Acetato-0:0')bis- 3,5-dichloro-2-[(phenylimino)methyl]phenyl-C,N]dipalladium (8.29 g, 10 mmole) and triphenylphosphine (21.0 g, 80 mmole) in dry benzene (150 ml) was stirred for 30 minutes at ambient temperature under $N_2$. The 4-fluorophenylmagnesium bromide, prepared from 4-bromofluorobenzene (15.4 g, 88 mmole) and magnesium (1.94 g, 80 mmole) in dry ether (100 ml) under $N_2$ at ambient temperature, was added to the above solution in one portion. The resulting mixture was stirred for one hour at ambient temperature. After the addition of 6 N HCL (50 ml) with stirring for one hour, the mixture was filtered. The filtrate was diluted with ether (300 ml) and washed with brine (2×100 ml). The organic layer was refiltered to remove more yellow solid and the filtrate, washed with brine (2×100 ml), dried over $MgSO_4$, filtered and evaporated. The residue was chromato-

| Grignard Reagent | End Product | mp °C. | Calc. | Found |
|---|---|---|---|---|
| phenyl | (E)-trans-6-[2-(3,5-di-chloro-2-[1,1'-biphenyl]-yl)ethenyl]-3,4,5,6-tetra-hydro-4-hydroxy-2H-pyran-2-one | 113–115° | C 62.83<br>H 4.44 | C 62.47<br>H 4.64 |
| 4-chlorophenyl | (E)-trans-6-[2-(3,4',5-trichloro-2-[1,1'-biphenyl]-yl)ethenyl]-3,4,5,6-tetra-hydro-4-hydroxy-2H-pyran-2-one | 116.5–118° | C 57.38<br>H 3.80 | C 57.07<br>H 3.85 |

EXAMPLE 34

Alternate Preparation of 3,5-Dichloro-4'-fluoro-[1,1'-biphenyl]-2-carboxaldehyde

Step A. Preparation of Bis[μ-(Acetato-0:0')bis-3,5-dichloro-2[(phenylimino)-methyl]phenyl C,N]dipalladium A mixture of N-[(2,4-Dichlorophenyl)methylene]-benzeneamine (2.5 g, 10 mmole) and palladium (II) acetate (2.24 g, 10 mmole) in acetic acid (50 ml) was heated at reflux for one hour with stirring. The turbid solution was filtered and the filtrate was diluted with water (300 ml) to give the title compound as a red solid (3.9 g, 94%). Crystallization from acetic acid-water (7:1, v:v) provided an analytical sample of the title comgraphed on a silica column (1000 g). Elution with ether-hexane (1:39, v:v, 5500 ml) provided a forerun which was discarded. Continued elution with ether-hexane (1:9, v:v, 5700 ml) gave the title compound as a yellow solid (4.5 g, 84%), mp 73°–74° C.: pmr $(CDCl_3)\delta$ 7.03–7.40 (5H, m), 7.53 (H, d, J=1.5 Hz), 10.13 (H,S).

EXAMPLE 35

Starting with bis[μ-(Acetato-0:0') bis-3,5-dichloro-2[(phenylimino)methyl]phenyl-C,N]dipalladium but substituting equal amounts of the following Grignard reagents for 4-fluorophenylmagnesium bromide in Step B of Example 34 and following the procedure of Step B there was obtained a corresponding amount of the appropriate end product listed below.

EXAMPLE 35

| GRIGNARD | PRODUCT | pmr (δ) |
|---|---|---|
| 3-methylphenyl | 3,5-dichloro-3'-methyl-[1,1'-biphenyl]-2-carboxaldehyde | 2.3(3H.S), 7.0–7.8 (6H,m), 9.8 (H,s) |
| 3,5-dimethylphenyl | 3,5-dichloro-3',5'-dimethyl-[1,1'-biphenyl]-2-carboxaldehyde | 2.3(6H,s), 6.7–7.5 (5H,m), 10.0(H,s) |
| 4-fluoro-2-methyl phenyl | 3,5-dichloro-4'-fluoro-2'-methyl-[1,1'-biphenyl]-2-carboxaldehyde | 2.0(3H,s), 6.9–7.5 (5H,m), 10.1(H,s) |
| 3-ethylphenyl | 3,5-dichloro-3'-ethyl-[1,1'-biphenyl]-2-carboxaldehyde | 1.4(3H,t) 2.9(2H,q), 7.2–7.6 (6H,m), 10.0 (H,s) |
| 4-fluoro-3-methyl phenyl | 3,5-dichloro-4'-fluoro-3'-methyl-[1,1'-biphenyl]- | 2.3(3H,s), 7.0–7.5(5H,m) 10.1(H,s) |

EXAMPLE 35-continued

| GRIGNARD | PRODUCT | pmr (δ) |
|---|---|---|
| 3,4-dichlorophenyl | 2-carboxaldehyde 3,3',4',5-tetrachloro-[1,1'-biphenyl]-2-carboxaldehyde | 7.0–7.6(5H,m), 10.3(H,s) |
| 3,5-dichlorophenyl | 3,3',5,5'-tetrachloro-[1,1'-biphenyl]-2-carboxaldehyde | 7.1–7.6(5H,m), 10.3(H,s) |
| 2-methylphenyl | 3,5-dichloro-2'-methyl-[1,1'-biphenyl]-2-carboxaldehyde | 2.1(3H,s), 7–7.6 (6H,m), 10.0(H,s) |
| 3-methoxyphenyl | 3,5-dichloro-3'-methoxy-[1,1'-biphenyl]-2-carboxaldehyde | 3.9(3H,s), 6.8–7.6 (6H,m), 10.1(H,s) |
| 4-methylphenyl | 3,5-dichloro-4'-methyl-[1,1', biphenyl]-2-carboxaldehyde | 2.40 (3H,S), 7.13–7.40 (5H, m), 7.50 (H, d, J = 1.5Hz), 10.06 (H, S) |
| 4-methoxyphenyl | 3,5-dichloro-4'-methoxy-[1,1'-biphenyl]-2-carboxaldehyde | 3.85 (3H, S), 6.93–7.50 (6H, m), 10.03 (H, S) |
| 3-fluorophenyl | 3,5-dichloro-3'-fluoro-[1,1'-biphenyl]-2-carboxaldehyde | 6.93–7.60 (6H, m), 10.16 (H, S) |

EXAMPLE 36

5-chloro-4'-Fluoro-3,3'-dimethyl-[1,1'-biphenyl]-2-carboxaldehyde

Step A: Preparation of N- [4-chloro-2-methyl (phenyl) methylene]-benzeneamine

A mixture of 4-chloro-2-methylbenzaldehyde (3.5 g, 22.6 mmol) and aniline (2.11 g, 22.6 mmol) in toluene (40 ml) was heated at reflux in a Dean-Stark apparatus for 1 hour. The mixture was cooled and evaporated in vacuo to leave an oily residue. The residue was redissolved in ether, washed with 5% sodium bicarbonate solution. The organic phase was separated, dried over MgSO$_4$ and filtered. The filtrate was concentrated in vacuo to afford an oily residue which was purified by distillation via a Kugelrohr apparatus (oven temperature 160° C., 0.5 mm) to provide the title compound (4.0 g, 7.4 mmol, 77%) as a viscous oil; pmr (CDCl$_3$)δ2.5(3H, s), 6.3–7.5(7H,m), 7.95(H, d), 8.6(H,s).

Step B. Preparation of 5-chloro-4'-fluoro-3,3'-dimethyl [1,1'-biphenyl]-2-carboxaldehyde By substituting an equimolar amount of N-[(4-chloro-2-methylphenyl)methylene]benzeneamine in place of N-[(2,4-dichlorophenyl)methylene]benzeneamine in step A of example 34 and replacing the 4-fluophenylmagnesium bromide with an equimolar amount of 4-fluoro-3-methylphenylmagnesium bromide) in Step B of example 34 and following the procedures described therein, there was obtained a corresponding amount of the title compound; pmr (CDCl$_3$)δ2.30(3H,d), 2.60(3H,s), 7.1 7.3 (5H,m), 9.9 (H,s).

EXAMPLE 37

3',4'-Dichloro-3,5-dimethyl-[1,1'-biphenyl]-2-carboxaldehyde

By substituting an equimolar amount of N-[(2,4-dimethylphenyl)methylene]benzeneamine in place of N-[(2,4-dichlorophenyl)methylene]benzeneamine in Step A of Example 34 and replacing the 4-fluorophenylmagnesium bromide with an equimolar amount of 3,4-dichlorophenylmagnesium bromide in Step B of Example 34 and following the procedures described therein, there was obtained a corresponding amount of the title compound, mp 80°–81° C.; pmr(CDCl$_3$)δ2.4(3H,s), 2.6(3H,s), 7.0–7.5(5H,m), 10.0(H,s).

Analysis Calc. for $C_{15}H_{12}Cl_2O$: C, 64.54 H, 4.33; Found: C, 64.83 H, 4.45

EXAMPLE 38

Employing the procedure substantially as described in Example 37, but substituting for the 3,4-dichlorophenylmagnesium bromide used therein, an equimolecular amount of the Grignard reagents listed below there were prepared the corresponding substituted biphenyl-2-carboxaldehydes.

| GRIGNARD | PRODUCT | pmr(δ) |
|---|---|---|
| 4-fluoro-3-methyl-phenyl | 4'-fluoro-3,3',5-trimethyl-[1,1'-biphenyl]-2-carboxaldehyde | 2.4(3H,d), 2.5(3H,s), 2.7(3H,s), 7.0–7.3(5H,m), 9.9(1H,s) |
| 3,5-dimethylphenyl | 3,3',5,5'-tetramethyl-[1,1'-biphenyl]-2-carboxaldehyde | 2.3(9H,m), 2.6(3H,s) 6.8–7.0(5H,m) 10.0(1H,s) |
| 4-Fluorophenyl | 4'fluoro-3,5-dimethyl-[1,1'-biphenyl]-2-carboxaldehyde | 2.4(3H,s),26(3H,s), 7.0–7.4(6H,m), 10.0(1H,s) |
| 4-Fluoro-3,5-dimethyl-phenyl | 4'-fluoro-3,3'5,5'-tetramethyl-[1,1'-biphenyl]-2-carboxaldehyde | 2.3(6H,d), 2.4(3H,s), 2.6(3H,s), 6.8–7.1(4H,m), 10.0(1H,s) |

EXAMPLE 39

3',4'-Dichloro-3,6-dimethyl-[1,1'-biphenyl]-2-carboxaldehyde

By substituting an equimolar amount of N-[(2,5-dimethylphenyl)methylene]benzeneamine in place of N-[(2,4-dichlorophenyl)methylene]benzeneamine in Step A of Example 34 and replacing the 4-fluorophenylmagnesium bromide with an equimolar amount of 3,4-dichlorophenylmagnesium bromide in Step B of Example 34 and following the procedures described therein, there was obtained a corresponding amount of the title compound as a pale yellow gum; pmr (CDCl$_3$) δ2.0 (3H,s), 2.6 (3H,s), 7.0–7.6 (5H,m), 9.9 (H,s).

EXAMPLE 40

3-Chloro-4'-fluoro-3'-methyl-[1,1'-biphenyl]-2-carboxaldehyde

Step A: Preparation of N-[(2-chlorophenyl)methylene]benzeneamine

When the procedure of Example 36 Step A, is followed, except that an equimolar quantity of 2-chlorobenzaldehyde is used in place of 4-chloro-2-methylbenzaldehyde, there is obtained the title compound as a viscous oil.

Anal. Calc'd. for C$_{13}$H$_{10}$ClN: %C, 72.40; %H, 4.67, %N, 6.49. Found: %C, 72.35, %H, 5.02, %N, 6.46.

Step B: Preparation of 3-chloro-4'-fluoro-3'-methyl-[1,1'-biphenyl]-2-carboxaldehyde By substituting a equimolar quantity of N-[(2-chlorophenyl)methylene]benzeneamine in place of N-[(2,4-dichlorophenyl)methylene]benzeneamine in Step A of Example 34 and replacing the 4-fluorophenylmagnesium bromide with an equimolar amount of 4-fluoro-3-methylphenylmagnesium bromide in Step B of Example 34 and following the procedures described therein, there is obtained the title compound, mp 74°–79° C.

Anal. Calc'd for C$_{14}$H$_{10}$ClFO: %C, 67.62; %H, 4.05. Found: %C, 67.83, %H, 4.09.

EXAMPLE 41

By substituting an equimolar amount of the following aldehydes for 2,4-dichloro-6-phenylmethoxybenzaldehyde in alternate to alternate Step B, Example 1, and then following Steps B through F of Example 1, the corresponding tetrahydropyran-2H-ones listed below were obtained.

EXAMPLE 41

| Starting Aldehyde | End Product | mp | Analysis Calcd | | Found | |
|---|---|---|---|---|---|---|
| 3,5-dichloro-4'-methyl-[1,1'-biphenyl]-2-carboxaldehyde | (E)-trans-6-{2-(3,5-dichloro-4'-methyl-2-[1,1'-biphenyl]yl)-ethenyl}-3,4,5,6-tetrahydro-4-hydroxy-2H-pyran-2-one | 119°–119.5°. | C: 63.67 H: 4.81 | | 63.69 4.88 | |
| 3,5-dichloro-4'-methoxy-[1,1'-biphenyl]-2-carboxaldehyde | (E)-trans-6-{2-(3,5-dichloro-4'-methoxy-2-[1,1'-biphenyl]yl)-ethenyl}-3,4,5,6-tetrahydro-4-hydroxy-2H-pyran-2-one | 100°–102° | C: 61.08 H: 4.61 | C: H: | 60.95 4.65 | |
| 3,5,-dichloro-3'-fluoro-[1,1'-biphenyl]-2-carboxaldehyde | (E)-trans-6-{2-(3,5-dichloro-3'-fluoro-2-[1,1'-biphenyl]yl)-ethenyl}-3,4,5,6-tetrahydro-4-hydroxy-2H-pyran-2-one | 130°–132° | C: 59.86 H: 3.97 | | 59.75 3.94 | |
| 3',4'-dichloro-3,5-dimethyl-[1,1'-biphenyl]-2-carboxaldehyde | (E)-trans-6-[2-(3',4'-dichloro-3,5-dimethyl-2-[1,1'-biphenyl]yl)ethenyl]-3,4,5,6-tetrahydro-4-hydroxy-2H-pyran-2-one | 128–129° | C: 64.46 H: 5.15 | C: H: | 64.11 5.16 | |
| 3,5-dichloro-3'-methyl-[1,1'-biphenyl]-2-carboxaldehyde | (E)-trans-6-[2-(3,5-dichloro-3'-methyl-2-[1,1'-biphenyl]yl)ethenyl]-3,4,5,6-tetrahydro-4-hydroxy-2H-pyran-2-one 0.05M CHCl$_3$ Solvate | glass | C: 62.84 H: 4.75 | C: H: | 62.60 4.82 | |
| 3,5-dichloro-3',5'-dimethyl-[1,1'-biphenyl]-2-carboxaldehyde | (E)-trans-6-[2-(3,5-dichloro-3',5'-dimethyl-2-[1,1'-biphenyl]yl)ethenyl]-3,4,5,6-tetrahydro-4-hydroxy-2H-pyran-2-one 0.05M CHCl$_3$ Solvate | glass | C: 63.60 H: 5.09 | C: H: | 63.99 5.26 | |
| 3',4'-dichloro-3,6-dimethyl-[1,1'-biphenyl]-2-carboxaldehyde | (E)-trans-6[2-(3',4'-dichloro-3,6-dimethyl-2-[1,1'-biphenyl]yl)ethenyl]-3,4,5,6-tetrahydro-4-hydroxy-2H-pyran-2-one | glass | C: 64.46 H: 5.15 | C: H: | 64.39 5.33 | |
| 3,5-dichloro-2'-methyl-[1,1'-biphenyl]-2-carboxaldehyde | (E)-trans-6-[2-(3,5-dichloro-2'-methyl-2-[1,1' biphenyl]yl)-ethenyl]-3,4,5,6-tetrahydro-4-hydroxy-2H-pyran-2-one | 140–141° | C: 63.67 H: 4.81 | C: H: | 64.04 4.92 | |
| 3,5-dichloro-4'-fluoro-2'-methyl-[1,1'-biphenyl]-2-carboxaldehyde | (E)-trans-6-[2-(3,5-dichloro-4'-fluoro-2'-methyl-2-[1,1'-biphenyl]yl)-ethenyl]-3,4,5,6-tetrahydro-4-hydroxy-2H-pyran-2-one | glass | C: 60.77 H: 4.33 | C: H: | 60.99 4.36 | |
| 3,5-dichloro-3'-ethyl-[1,1'-biphenyl]-2-carboxaldehyde | (E)-trans-6-[2-(3,5-dichloro-3'-ethyl-2-[1,1'-biphenyl]yl)ethenyl]-3,4,5,6-tetrahydro-4-hydroxy- | gum | C: 63.64 H: 5.09 | C: H: | 63.28 5.19 | |

EXAMPLE 41-continued

| Starting Aldehyde | End Product | mp | Analysis Calcd | | Found | |
|---|---|---|---|---|---|---|
| 3,3',4',5-tetra-chloro-[1,1'-biphenyl]-2-carboxaldehyde | 2H-pyran-2-one 0.05M CHCl₃ Solvate (E)-trans-6-[2-(3,3',4',5-tetrachloro-2-[1,1'-biphenyl]yl)-ethenyl]-3,4,5,6-terahydro-4-hydroxy-2H-pyran-2-one | glass | C: | 52.81 | C: | 3.27 |
| | | | H: | 52.49 | H: | 3.35 |
| 3,3',5,5'-tetra-chloro-[1,1'-biphenyl]-2-carboxaldehyde | (E)-trans-6-[2-(3,3',5,5'-tetrachloro-2-[1,1'-biphenyl]yl)-ethenyl]-3,4,5,6-tetrahydro-4-hydroxy-2H-pyran-2-one | glass | C: | 52.81 | C: | 52.73 |
| | | | H: | 3.27 | H: | 3.37 |
| 3,5-dichloro-4'-fluoro-3'-methyl-[1,1'-biphenyl]2-carboxaldehyde | (E)-trans-6-[2-(3,5-dichloro-4'-fluoro-3'-methyl-2-[1,1'-biphenyl]yl)-ethenyl]-3,4,5,6-tetrahydro-4-hydroxy-2H-pyran-2-one 0.1MCHCl₃ Solvate | glass | C: | 59.29 | C: | 54.29 |
| | | | H: | 4.23 | H: | 4.27 |
| 3,5-dichloro-3'-methoxy-[1,1'-biphenyl]-2-carboxaldehyde | (E)-trans-6-[2-(3,5-dichloro-3'-methoxy-2-[1,1'-biphenyl]yl)-ethenyl]-3,4,5,6-tetrahydro-4-hydroxy-2H-pyran-2-one | 93–4° | C: | 61.08 | C: | 61.26 |
| | | | H: | 4.61 | H: | 4.79 |
| 4'-fluoro-3,3',5-trimethyl-[1,1'-biphenyl]-2-carboxaldehyde | (E)-trans-6-[2-(4'-flouro-3,3',5-trimethyl-2-[1,1'-biphenyl]yl)ethenyl]-3,4,5,6-tetrahydro-4-hydroxy-2H-pyran-2-one | 115–116 | C: | 74.56 | C: | 74.79 |
| | | | H: | 6.54 | H: | 6.84 |
| 3,3',5,5'-tetramethyl-[1,1'-biphenyl]-2-carboxaldehyde | (E)-trans-6-[3,3',5,5'-tetramethyl-2-[1,1'-biphenyl]-yl)ethenyl)-3,4,5,6-tetrahydro-4-hydroxy-2H-pyran-2-one | 109–110 | C: | 78.83 | C: | 79.02 |
| | | | H: | 7.48 | H: | 7.79 |
| 4'fluoro-3,5-dimethyl-[1,1'-biphenyl]-2-carboxaldehyde | (E)-trans-6[2-(4'-fluoro 3,5-dimethyl-2-[1,1'-biphenyl]yl)-ethenyl]-3,4,5,6-tetrahydro-4-hydroxy-2H-pyran-2-one | 154–156° | C: | 74.10 | C: | 74.50 |
| | | | H: | 6.22 | H: | 6.57 |
| 3-chloro-4'-fluoro-3'-methyl-[1,1'-biphenyl]-2-carboxaldehyde | (E)-trans-6-[2-(3-chloro-4'-fluoro-3'-methyl-2-[1,1'-biphenyl]-yl)ethenyl]-3,4,5,6-tetrahydro-4-hydroxy-2H-pyran-2-one | glass | | | | |
| 5-chloro-4'-fluoro-3,3'-dimethyl-[1,1'-biphenyl]-2-carboxaldehyde | (E)-trans-6-[2-(5-chloro-4'-fluoro-3,3'-dimethyl-2-[1,1'-biphenyl]yl)-ethenyl]-3,4,5,6-tetra-hydro-4-hydroxy-2H-pyran-2-one | 109–110° | C: | 67.29 | C: | 67.33 |
| | | | H: | 5.38 | H: | 5.42 |
| 4'-fluoro-3,3',5,5'-tetramethyl-[1,1'-biphenyl]-2-carboxaldehyde | (E)-trans-6-[2-(4'-fluoro-3,3'5,5'-tetramethyl-2-[1,1'-biphenyl]-yl)ethenyl]-3,4,5,6-tetrahydro-4-hydroxy-2H-pyran-2-one | 142–146° | C: | 74.98 | C: | 75.20 |
| | | | H: | 6.84 | H: | 7.23 |

EXAMPLE 42

Resolution of the Optical Isomers of (±) Trans-6-{2-[2,4-dichloro-6-(4-fluorophenylmethoxy)-phenyl]ethyl}-3,4,5,6-tetrahydro-4-hydroxy-2H-pyran-2-one.

Step A. Preparation and Separation of the Diastereomeric Amides (Diastereomers A and B)

A solution of (±)-trans-6-{2-[2,4-dichloro-6-(4-fluorophenylmethoxy)phenyl]ethyl}-3,4,5,6-tetrahydro-4-hydroxy-2H-pyran-2-one (28.3 g, 68 mmole) and 1-(−)-α-methylbenzylamine (16.5 g, 136 mmole) in tetrahydrofuran (350 ml) was refluxed for 20 hours. The tetrahydrofuran was removed in vacuo and the residue was stirred in ether (500 ml) and the precipitate collected to give diastereomer A which was twice stirred for 15 min. in refluxing ether (500 ml) to yield a colorless solid (13.0 g, 36%) which melted at 185°–188° C.

Step B. Preparation of (+) Trans-6-{2-[2,4-dichloro-6-(4-fluorophenylmethoxy)-phenyl]ethyl}-3,4,5,6-tetrahydro-4-hydroxy-2H-pyran-2-one By substituting an equimolar amount of diastereomer A from Step A above for diastereomer A in Step B of Example 13 and following the procedures described therein, there was obtained a corresponding amount of the title compound which was recrystallized from n-butylchloride-pet ether (4:3, v:v), mp 133°–135° C., pmr (CDCl₃) δ1.53–2.20 (5H, m); 2.66 (2H, m), 2.93 (2H, m), 4.36 (H, m), 4.73 (H, m), 5.04 (2H, s), 6.85 (H, d), 7.03–7.53 (5H, m).

Analysis Calc. for $C_{20}H_{19}Cl_2FO_4$: Calc: C, 58.12; H, 4.63; Found: C, 58.25; H, 4.71

$[\alpha]_D^{25}$ +17.8° (C, 1.0; chloroform)

EXAMPLE 43

Preparation of
(+)-(E)-(3R*,5S*)-7-(3,5-dichloro-4'-fluoro[1,1'-biphenyl]-2-yl)-3,5-dihydroxy-6-heptenoic acid, ammonium salt.

Step A. Preparation and Separation of Diastereomeric Amides

By substituting an equimolar amount of (±)-trans-(E)-6-{2-[3,5-dichloro-4'-fluoro[1,1'-biphenyl]-2-yl)ethenyl}-3,4,5,6-tetrahydro-4-hydroxy-2H-pyran-2-one for (±)-trans-6-{2-[2,4-dichloro-6-(4-fluorophenylmethoxy)phenyl]ethyl}-3,4,5,6-tetrahydro-4-hydroxy-2H-pyran-2-one in Step A of Example 42 and following the procedure described therein there was obtained a corresponding amount of Diastereomer A as colorless crystals which melted at 128.5°–129° C.

Step B. Preparation of
(+)-(E)-(3R*,5S*)-7-{3,5-dichloro-4'-fluoro[1,1'-biphenyl]-2-yl}-3,5-dihydroxy-6-heptenoic acid, ammonium salt Diastereomer A (6.2 g, 12.3 mmole) of Step A was dissolved in 95% ethanol (600 ml) containing 1 N NaOH (60 ml, 60 mmole) and the solution was refluxed for 16 hours. The solvent was removed in vacuo and the residue was suspended in ice water (200 ml) and ether (500 ml) and subsequently acidified with 3 N HCl (50 ml). The ether layer was washed successively with ice-cold 1 N HCl (200 ml), brine (2×200 ml), dried over MgSO$_4$, and filtered. Anhydrous ammonia was bubbled through the cold etherial solution for 2 min. Vigorous stirring was then continued at 20° C. for 1 hour and then the mixture was cooled slowly to ca 5° C. Filtration provided the title compound as tiny colorless needles (4.3 g, 84%), mp 105°–108° C. dec. pmr (d$_6$-DMSO) δ1.15 (H, m), 1.41 (H, m), 1.99 (H, dd), 2.14 (H, dd), 3.66 (H, m), 4.11 (H, dd), 5.52 (H, dd) 6.38 (H, d), 7.23–7.42 (5H, m), 7.69 (H, d).

Analysis for C$_{19}$H$_{20}$Cl$_2$FNO$_4$: Calc: C, 54.82 H, 4.84 N, 3.36; Found: C, 55.13 H, 4.98 N, 3.07

$[\alpha]_D^{27} = +10.75°$ (C, 1.6; water)

Employing the procedure of Example 43 the other 6-(biphenylethenyl)-3,4,5,6-tetrahydro-4-hydroxy-2H-pyran-2-ones of Example 41 are resolved into their dextro- and levoratatory enantiomers, the 4(R)-enantiomer (usually the dextrorotatory) having the antihypercholesterolemic activity.

What is claimed is:

1. A compound of structural formula

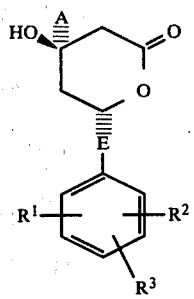

wherein
A is H or methyl;
E is —CH=CH—, or —CH$_2$CH$_2$—;
R$_1$, R$_2$ and R$_3$ are each selected from
halogen,
C$_{1-4}$alkyl,
C$_{1-4}$haloalkyl,
substituted phenyl in which the substituents are
halo,
C$_{1-4}$alkyl, or
C$_{1-4}$alkoxy, and
R$_4$O in which R$_4$ is
phenyl,
halophenyl, or
substituted phenyl-C$_{1-3}$alkyl wherein the substituents are selected from halogen and C$_{1-4}$haloalkyl;
all of the compounds being the enantiomer having a 4 (R) configuration in the tetrahydropyran moiety of the trans racemate.

2. The compound of claim 1 wherein:
A is H or methyl;
E is —CH$_2$CH$_2$— or —CH=CH—;
R$_1$ is in the 6-position and is substituted phenyl, wherein there are 1 or 2 substituents independently selected from chloro, fluoro, methyl and methoxy; and
R$_2$ and R$_3$ are independently halo, or C$_{1-3}$ alkyl in the 2- and 4-positions
all of the compounds being the enantiomer having a 4 (R) configuration in the tetrahydropyran moiety of the trans racemate.

3. The compound of claim 1, or 2 wherein A is hydrogen.

4. The compound of claim 3, wherein E is —CH=CH—.

5. The compound of claim 4 which is the 4 (R)-trans-enantiomer of:
6-[2-(3,5-dichloro-4'-fluoro[1,1'-biphenyl]-2-yl)ethenyl]-3,4,5,6-tetrahydro-4-hydroxy-2H-pyran-2-one;
6-[2-(3,3',5-trimethyl-4'-fluoro[1,1'-biphenyl]-2-yl)ethenyl]-3,4,5,6-tetrahydro-4-hydroxy-2H-pyran-2-one;
6-[2-(3,3'-dimethyl-4'-fluoro-5-chloro[1,1'-biphenyl]-2-yl)ethenyl]-3,4,5,6-tetrahydro-4-hydroxy-2H-pyran-2-one; or
6-[2-(3,3'5,5'-tetramethyl[1,1'-biphenyl]-2-yl)ethenyl]-3,4,5,6-tetrahydro-4-hydroxy-2H-pyran-2-one.

6. A hypocholesterolemic, hypolipemic, pharmaceutical composition comprising a pharmaceutical carrier and an effective hypocholesterolemic, hypolipemic amount of a compound of structural formula:

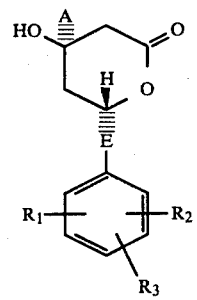

wherein
A is H of methyl;
E is —CH=CH—, or —CH$_2$CH$_2$—;
R$_1$, R$_2$ and R$_3$ are each selected from halogen,
C$_{1-4}$alkyl,
C$_{1-4}$haloalkyl,
substituted phenyl in which the substituents are
  halo,
  C$_{1-4}$alkyl, or
  C$_{1-4}$alkoxy, and
R$_4$O in which R$_4$ is
  phenyl,
  halophenyl, or
  substituted phenyl-C$_{1-3}$alkyl wherein the substituents are selected from halogen and C$_{1-4}$ haloalkyl;
all of the compounds being the enantiomer having a 4 (R) configuration in the tetrahydropyran moiety of the trans racemate.

7. The pharmaceutical composition of claim 6 wherein:
A is H or methyl;
E is —CH$_2$CH$_2$— or —CH=CH—;
R$_1$ is in the 6-position and is substituted phenyl, wherein there are 1 or 2 substituents independently selected from chloro, fluoro, methyl or methoxy; and
R$_2$ and R$_3$ are independently halo, or C$_{1-3}$ alkyl in the 2- and 4-positions
all of the compounds being the enantiomer having a 4 (R) configuration in the tetrahydropyran moiety of the trans racemate.

8. The pharmaceutical composition of claim 6 or 7 wherein A is hydrogen.

9. The pharmaceutical composition of claim 8, wherein E is —CH=CH—.

10. The pharmaceutical composition of claim 9 which is the 4(R)-trans-enantiomer of:
6-[2-(3,5-dichloro-4'-fluoro[1,1'-biphenyl]-2-yl)ethenyl]-3,4,5,6-tetrahydro-4-hydroxy-2H-pyran-2-one;
6-[2-(3,3',5-trimethyl-4'-fluoro[1,1'-biphenyl]-2-yl)ethenyl]-3,4,5,6-tetrahydro-4-hydroxy-2H-pyran-2-one;
6-[2-(3,3'-dimethyl-4'-fluoro-5-chloro[1,1'-biphenyl]-2-yl)ethenyl]-3,4,5,6-tetrahydro-4-hydroxy-2H-pyran-2-one; or
6-[2-(3,3',5,5'-tetramethyl[1,1'-biphenyl]-2-yl)ethenyl]-3,4,5,6-tetrahydro-4-hydroxy-2H-pyran-2-one.

11. A method of inhibiting cholesterol biosynthesis comprising the administration to a patient in need of such treatment of an effective cholesterol biosynthesis inhibiting amount of a compound having the structure:

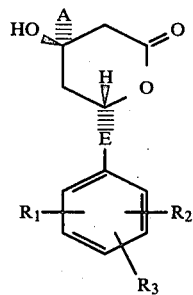

wherein
A is H or methyl;
E is —CH=CH—, or —CH$_2$CH$_2$—;
R$_1$, R$_2$ and R$_3$ are each selected from
  halogen;
  C$_{1-4}$alkyl,
  C$_{1-4}$haloalkyl,
  substituted phenyl in which the substituents are
    halo,
    C$_{1-4}$alkyl, or
    C$_{1-4}$alkoxy, and
  R$_4$O in which R$_4$ is
    phenyl,
    halophenyl, or
    substituted phenyl-C$_{1-3}$alkyl wherein the substituents are selected from halogen and C$_{1-4}$haloalkyl;
all of the compounds being the enantiomer having a 4 (R) configuration in the tetrahydropyran moiety of the trans racemate.

12. The method of claim 11 wherein:
A is H or methyl;
E is —CH$_2$CH$_2$— or —CH=CH—;
R$_1$ is in the 6-position and is substituted phenyl, wherein there are 1 or 2 substituents independently selected from chloro, fluoro, methyl and methoxy; and
R$_2$ and R$_3$ are independently halo, or C$_{1-3}$ alkyl in the 2- and 4-positions
all of the compounds being the enantiomer having a 4 R configuration in the tetrahydropyran moiety of the trans racemate.

13. The compound of claim 11 or 15 wherein A is hydrogen.

14. The method of claim 13, wherein E is —CH=CH—.

15. The method of claim 14 which is the 4(R)-trans-enantiomer of:
6-[2-(3,5-dichloro-4'-fluoro[1,1'-biphenyl]-2-yl)ethenyl]-3,4,5,6-tetrahydro-4-hydroxy-2H-pyran-2-one;
6-[2-(3,3',5-trimethyl-4'-fluoro[1,1'-biphenyl]-2-yl)ethenyl]-3,4,5,6-tetrahydro-4-hydroxy-2H-pyran-2-one;
6-[2-(3,3'-dimethyl-4'-fluoro-5-chloro[1,1'-biphenyl]-2-yl)ethenyl]-3,4,5,6-tetrahydro-4-hydroxy-2H-pyran-2-one; or
6-[2-(3,3'-5,5'-tetramethyl[1,1'-biphenyl]-2-yl)ethenyl]-3,4,5,6-tetrahydro-4-hydrox-2H-pyran-2-one.

16. The 4(R)-trans enantiomer of the compound 6-[2-(3,3',5-trimethyl-4'-fluoro-[1,1'-biphenyl]-2-yl)-ethenyl]-3,4,5,6-tetrahydro-4-hydroxy-2H-pyran-2-one of structural formula:

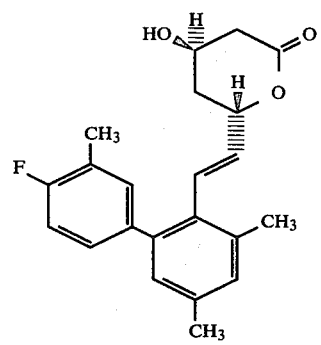

17. A hypocholesterolemic, hypolipemic, pharmaceutical composition comprising a pharmaceutical carrier and an effective hypocholesterolemic, hypolipemic amount of the 4(R)-trans enantiomer of the compound 6-[2-(3,3',-5-trimethyl-4'-fluoro[1,1'-biphenyl]-2-yl)-ethenyl]-3,4,5,6-tetrahydro-4-hydroxy-2H-pyran-2one of structural formula:

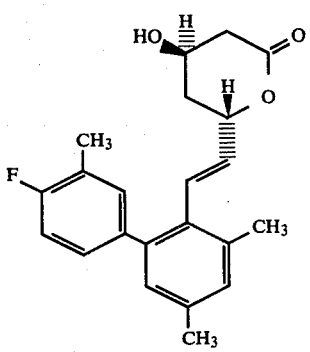

18. A method of inhibiting cholesterol biosynthesis comprising the administration to a patient in need of such treatment of an effective cholesterol biosynthesis inhibiting amount of 4(R)-trans enantiomer of the compound 6-[2-(3,3'-5-trimethyl-4'-fluoro[1,1'-biphenyl]-2-yl)-ethenyl]-3,4,5,6-tetrahydro-4-hydroxy-2H-pyran-2-one with structural formula:

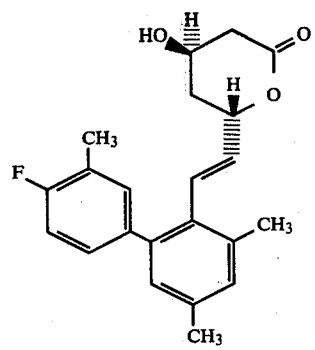

* * * * *